(12) United States Patent
Samelson et al.

(10) Patent No.: US 8,779,095 B2
(45) Date of Patent: Jul. 15, 2014

(54) LAT ADAPTER MOLECULE FOR ENHANCED T-CELL SIGNALING AND METHOD OF USE

(75) Inventors: Lawrence E. Samelson, Chevy Chase, MD (US); Lakshmi Balagopalan, Bethesda, MD (US)

(73) Assignee: The United States of America, as represented by the Secretary, Department of Health & Human Services, Washington, DC (US)

( * ) Notice: Subject to any disclaimer, the term of this patent is extended or adjusted under 35 U.S.C. 154(b) by 0 days.

(21) Appl. No.: 13/319,263

(22) PCT Filed: Apr. 30, 2010

(86) PCT No.: PCT/US2010/033186
§ 371 (c)(1),
(2), (4) Date: Nov. 7, 2011

(87) PCT Pub. No.: WO2010/129418
PCT Pub. Date: Nov. 11, 2010

(65) Prior Publication Data
US 2012/0114700 A1    May 10, 2012

Related U.S. Application Data

(60) Provisional application No. 61/176,231, filed on May 7, 2009.

(51) Int. Cl.
*C07K 14/435* (2006.01)
*C07K 14/47* (2006.01)
*A61K 35/14* (2006.01)

(52) U.S. Cl.
CPC .... *C07K 14/4705* (2013.01); *G01N 2333/7051* (2013.01); *A61K 35/17* (2013.01)
USPC ............................................................ 530/350

(58) Field of Classification Search
None
See application file for complete search history.

(56) References Cited

U.S. PATENT DOCUMENTS

| 7,118,889 B1 | 10/2006 | Samelson et al. |
| 2006/0073562 A1 | 4/2006 | Samelson et al. |
| 2007/0134749 A1 | 6/2007 | Samelson et al. |

FOREIGN PATENT DOCUMENTS

| WO | 9932627 A2 | 7/1999 |
| WO | 03068968 A2 | 8/2003 |

OTHER PUBLICATIONS

Lamothe et al., The Journal of Biological Chemistry, vol. 282, No. 6, pp. 4102-4112, Feb. 9, 2007.*
Tomlinson et al., Immunol Today. Nov. 2000;21(11):584-91.*
Zhang et al. (Cell, vol. 92, 83-92, Jan. 9, 1998, pp. 83-92).*
Houtman et al. (FEBS Journal 272 (2005) 5426-5435 2005 FEBS).*
Bunnell et al. (The Journal of Cell Biology, vol. 158, No. 7, Sep. 30, 2002 1263-1275).*
Bunnell et al. (Immunity. Mar. 2001;14(3):315-29).*
Zhang et al. (J Biol Chem. Jul. 28, 2000;275(30):23355-61).*
Balagopalan et al., "c-Cbl-Mediated Regulation of LAT-Nucleated Signaling Complexes", Molecular and Cellular Biology, vol. 27, No. 24, pp. 8622-8636 (2007).
Brignatz et al., "Evidences for ubiquitination and intracellular trafficking of LAT, the linker of activated T Cells", Biochimica et Biophysica Acta, vol. 1746, No. 2, pp. 108-115 (2005).
Aguado et al., "Activation of T lymphocytes and the role of the adapter LAT", Transplant Immunology, vol. 17, No. 1, pp. 23-26 (2006).
Wonerow et al., "The transplant adapter LAT plays a central role in immune receptor signalling", Oncogene, vol. 20, No. 44, pp. 6273-6283 (2001).
Hundt et al., "Impaired Activation and Localization of LAT in Anergic T Cells as a Consequence of a Selective Palmitoylation Defect", Immunity, vol. 24, No. 5, pp. 513-522 (2006).
Gringhuis et al., "Displacement of Linker for Activation of T Cells from the Plasma Membrane Due to Redox Balance Alterations Results in Hyperesponsiveness of Synovial Fluid T Lymphocytes in Rheumatoid Arthritis", Journal of Immunology, vol. 164, No. 4, pp. 2170-2179 (2000).
Lineberry et al., "T Cell Anergy: Where It's LAT", Immunity, vol. 24, No. 5, pp. 501-503 (2006).
Zeyda et al., "LAT Displacement from Lipid Rafts as a Molecular Mechanism for the Inhibition of T Cell Signalling by Polyunsaturated Fatty Acids", Journal of Biological Chemistry, vol. 277, No. 32, pp. 28418-28423 (2002).
Yi et al., "Specific and Potent RNA Interference in Terminally Differentiated Myotubes", Journal of Biological Chemistry, vol. 278, No. 2, pp. 934-939 (2003).
Cole et al., "Identification of MART-1-specific T-Cell Receptors: T Cells Utilizing Distinct T-Cell Receptor Variable and Joining Regions Recognize the Same Tumor Epitope", Cancer Research, vol. 54, No. 2, pp. 5265-5268 (1994).
Zhang et al., "Essential Role of LAT in T Cell Development", Immunity, vol. 10, No. 3, pp. 323-332 (1999).
Aguado et al., "Induction of T Helper Type 2 Immunity by a Point Mutation in the LAT Adapter", Science, vol. 296, pp. 2036-2040 (2002).
Jury et al., "Lipid rafts in T cell signalling and disease", Seminars in Cell & Developmental Biology, vol. 18, No. 5, pp. 608-615 (2007).

* cited by examiner

*Primary Examiner* — Zachary Skelding
(74) *Attorney, Agent, or Firm* — Edwards Wildman Palmer LLP; Peter F. Corless

(57) ABSTRACT

LAT (Linker for Activation of T-cells) is a protein involved in signaling through the T-cell receptor (TCR). The invention provides a LAT protein including mutations at ubiquitylation sites that result in an increase in stability of LAT in stimulated and unstimulated cells, and enhanced signaling through the TCR. The invention further provides use for a LAT protein including mutations at ubiquitylation sites for therapeutic and laboratory methods.

3 Claims, 16 Drawing Sheets

FIG. 6C
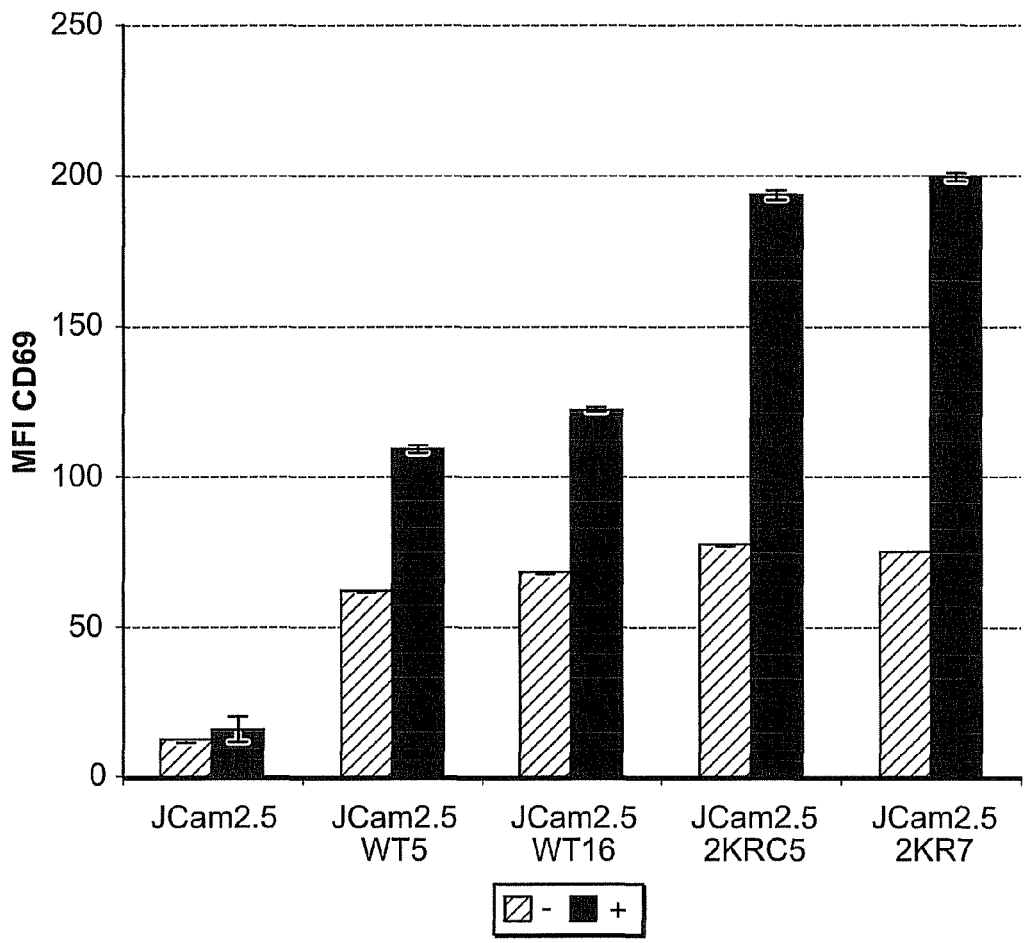
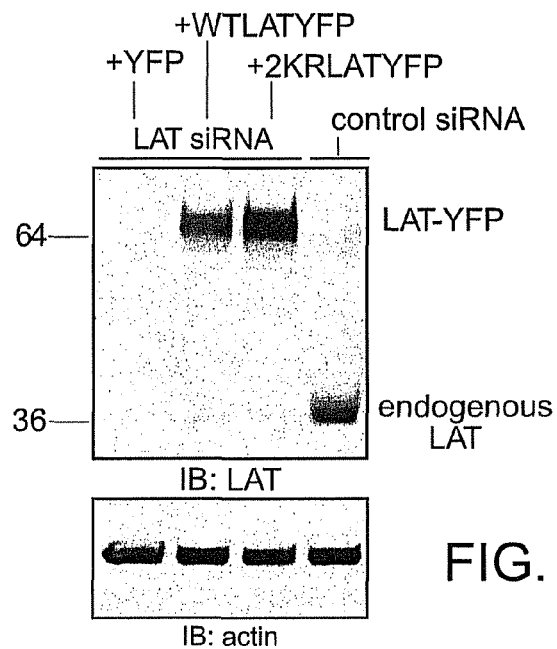
FIG. 7A

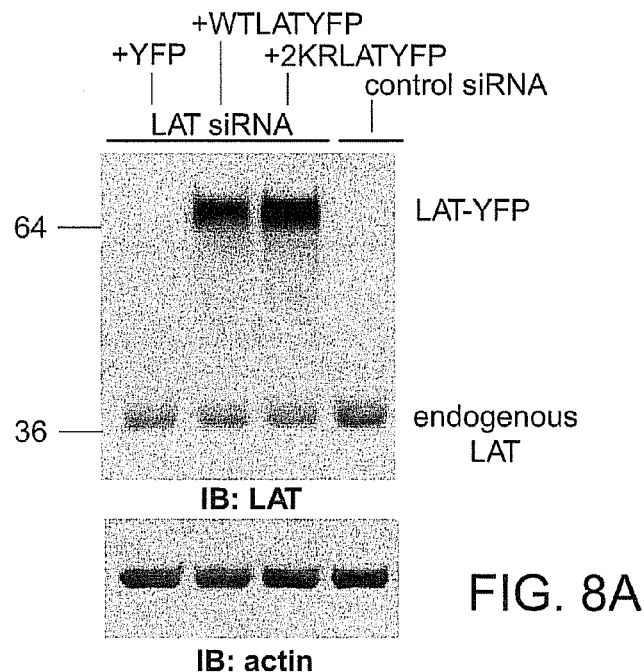
FIG. 8A
FIG. 8C
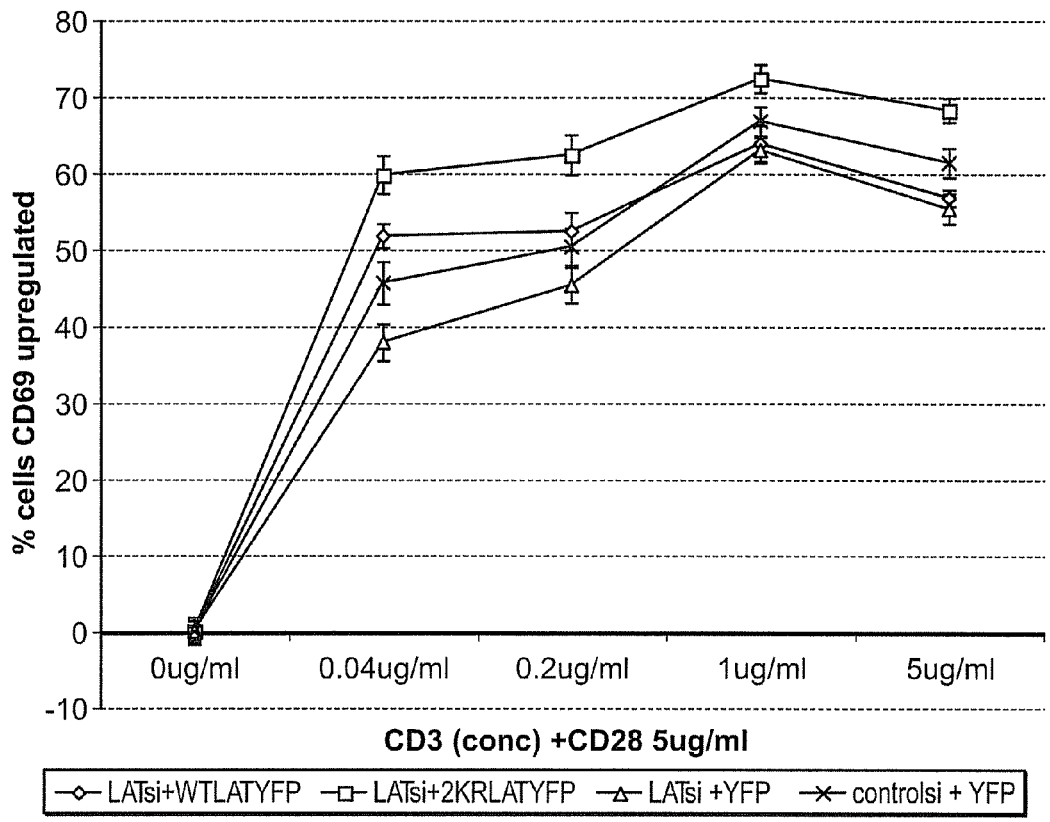

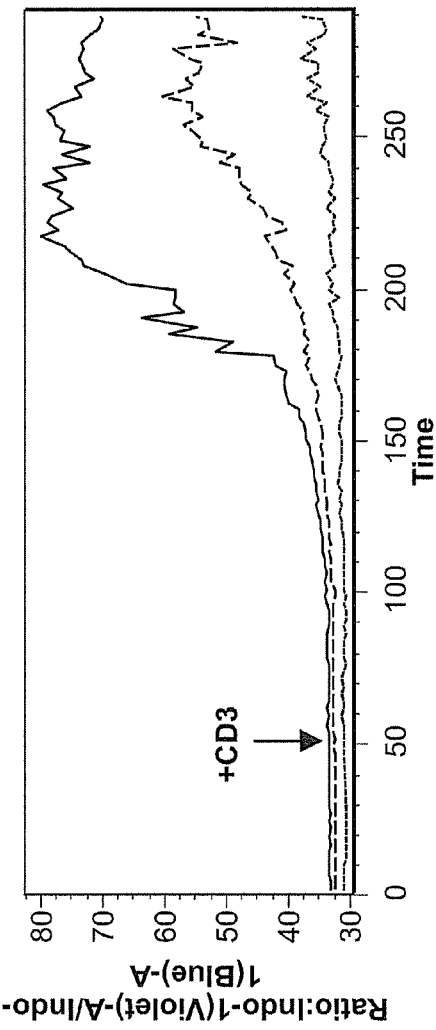
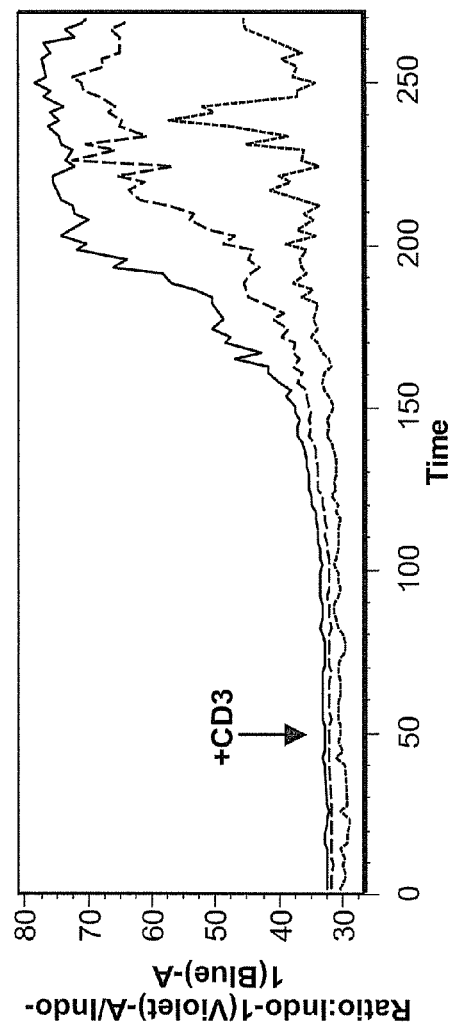
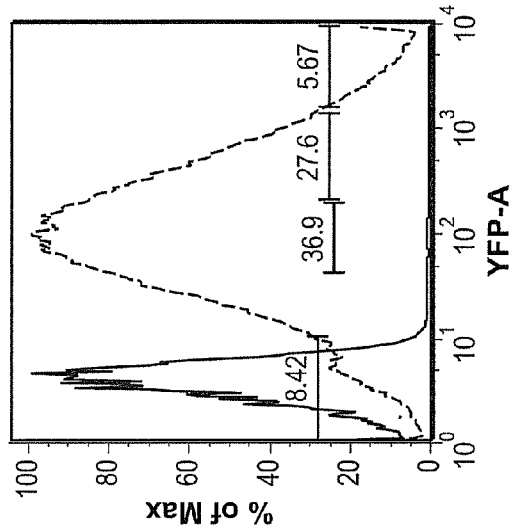
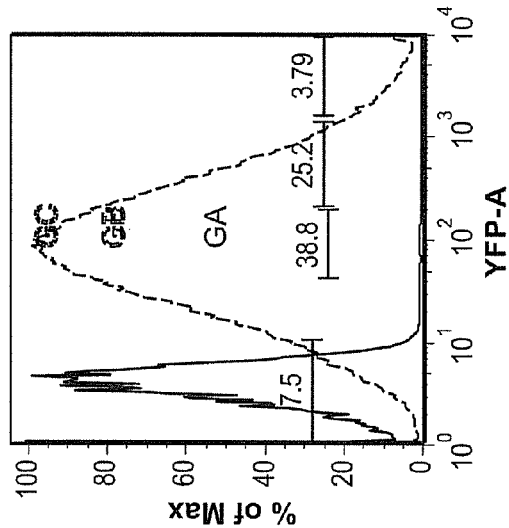

SEQUENCE LISTING

```
<160> NUMBER OF SEQ ID NOS: 14

<210> SEQ ID NO 1
<211> LENGTH: 233
<212> TYPE: PRT
<213> ORGANISM: Homo sapiens

<400> SEQUENCE: 1

Met Glu Glu Ala Ile Leu Val Pro Cys Val Leu Gly Leu Leu Leu Leu
1               5                   10                  15

Pro Ile Leu Ala Met Leu Met Ala Leu Cys Val His Cys His Arg Leu
            20                  25                  30

Pro Gly Ser Tyr Asp Ser Thr Ser Ser Asp Ser Leu Tyr Pro Arg Gly
        35                  40                  45

Ile Gln Phe Lys Arg Pro His Thr Val Ala Pro Trp Pro Pro Ala Tyr
    50                  55                  60

Pro Pro Val Thr Ser Tyr Pro Pro Leu Ser Gln Pro Asp Leu Leu Pro
65                  70                  75                  80

Ile Pro Arg Ser Pro Gln Pro Leu Gly Gly Ser His Arg Thr Pro Ser
                85                  90                  95

Ser Arg Arg Asp Ser Asp Gly Ala Asn Ser Val Ala Ser Tyr Glu Asn
            100                 105                 110

Glu Glu Pro Ala Cys Glu Asp Ala Asp Glu Asp Glu Asp Asp Tyr His
        115                 120                 125

Asn Pro Gly Tyr Leu Val Val Leu Pro Asp Ser Thr Pro Ala Thr Ser
    130                 135                 140

Thr Ala Ala Pro Ser Ala Pro Ala Leu Ser Thr Pro Gly Ile Arg Asp
145                 150                 155                 160

Ser Ala Phe Ser Met Glu Ser Ile Asp Asp Tyr Val Asn Val Pro Glu
                165                 170                 175

Ser Gly Glu Ser Ala Glu Ala Ser Leu Asp Gly Ser Arg Glu Tyr Val
            180                 185                 190

Asn Val Ser Gln Glu Leu His Pro Gly Ala Ala Lys Thr Glu Pro Ala
        195                 200                 205

Ala Leu Ser Ser Gln Glu Ala Glu Val Glu Glu Glu Gly Ala Pro
    210                 215                 220

Asp Tyr Glu Asn Leu Gln Glu Leu Asn
225                 230
```

<210> SEQ ID NO 2
<211> LENGTH: 242
<212> TYPE: PRT
<213> ORGANISM: Mus musculus

<400> SEQUENCE: 2

Met Glu Ala Asp Ala Leu Ser Pro Val Gly Leu Gly Leu Leu Leu Leu
1               5                   10                  15

Pro Phe Leu Val Thr Leu Leu Ala Ala Leu Cys Val Arg Cys Arg Glu
            20                  25                  30

Leu Pro Val Ser Tyr Asp Ser Thr Ser Thr Glu Ser Leu Tyr Pro Arg
        35                  40                  45

Ser Ile Leu Ile Lys Pro Pro Gln Ile Thr Val Pro Arg Thr Pro Ala
    50                  55                  60

Val Ser Tyr Pro Leu Val Thr Ser Phe Pro Pro Leu Arg Gln Pro Asp
65                  70                  75                  80

Leu Leu Pro Ile Pro Arg Ser Pro Gln Pro Leu Gly Gly Ser His Arg
                85                  90                  95

Met Pro Ser Ser Gln Gln Asn Ser Asp Asp Ala Asn Ser Val Ala Ser
            100                 105                 110

Tyr Glu Asn Gln Glu Pro Ala Cys Lys Asn Val Asp Ala Asp Glu Asp
        115                 120                 125

Glu Asp Asp Tyr Pro Asn Gly Tyr Leu Val Val Leu Pro Asp Ser Ser
    130                 135                 140

Pro Ala Ala Val Pro Val Val Ser Ser Ala Pro Val Pro Ser Asn Pro
145                 150                 155                 160

Asp Leu Gly Asp Ser Ala Phe Ser Val Glu Ser Cys Glu Asp Tyr Val
                165                 170                 175

Asn Val Pro Glu Ser Glu Glu Ser Ala Glu Ala Ser Leu Asp Gly Ser
            180                 185                 190

Arg Glu Tyr Val Asn Val Ser Pro Glu Gln Gln Pro Val Thr Arg Ala
        195                 200                 205

Glu Leu Ala Ser Val Asn Ser Gln Glu Val Asp Glu Gly Glu Glu
    210                 215                 220

Glu Gly Val Asp Gly Glu Glu Ala Pro Asp Tyr Glu Asn Leu Gln Glu
225                 230                 235                 240

Leu Asn

<210> SEQ ID NO 3
<211> LENGTH: 1680
<212> TYPE: DNA
<213> ORGANISM: Homo sapiens

<400> SEQUENCE: 3
caggcgggcg ggagggcggg cacggagagg cgggcgccga ggaggggcag gtagggctgg      60
gacgcagggg taactggatc ccccgacttc agcccaggcc ctggtctgac cacccctggga    120 gcagggactt tccacagtca gctggacgca cactcagccc agtaaaagag gggacccatc    180
ccgggagccc cggggagggc acagctgcct cctcccgggc tcccctgcca cctggtgcct    240
acctgccccc tgctccctgc cgggtccggt cctcacccca tcttcatctg gccttgactc    300
tgcccttgag gggcctaggg gtgcagccag cctgctccga gctcccctgc agatggagga    360
ggccatcctg gtccctgcg tgctgggggct cctgctgctg cccatcctgg ccatgttgat    420
ggcactgtgt gtgcactgcc acagactgcc aggctcctac gacagcacat cctcagatag    480

| | |
|---|---|
| tttgtatcca agggggcatcc agttcaaacg gcctcacacg gttgccccct ggccacctgc | 540 |
| ctacccacct gtcacctcct acccaccccct gagccagcca gacctgctcc ccatcccaag | 600 |
| atccccgcag ccccttgggg gctcccaccg gacgccatct tcccggcggg attctgatgg | 660 |
| tgccaacagt gtggcgagct acgagaacga ggaaccagcc tgtgaggatg cggatgagga | 720 |
| tgaggacgac tatcacaacc caggctacct ggtggtgctt cctgacagca ccccggccac | 780 |
| tagcactgct gccccatcag ctcctgcact cagcacccct ggcatccgag acagtgcctt | 840 |
| ctccatggag tccattgatg attacgtgaa cgttccggag agcggggaga gcgcagaagc | 900 |
| gtctctggat ggcagccggg agtatgtgaa tgtgtcccag gaactgcatc ctggagcggc | 960 |
| taagactgag cctgccgccc tgagttccca ggaggcagag aagtggagg aagaggggggc | 1020 |
| tccagattac gagaatctgc aggagctgaa ctgagggcct gtggaggccg agtctgtcct | 1080 |
| ggaaccaggc ttgcctggga cggctgagct gggcagctgg aagtggctct ggggtcctca | 1140 |
| catggcgtcc tgcccttgct ccagcctgac aacagcctga aaatcccccc cgtaacttat | 1200 |
| tatcactttg gggttcggcc tgtgtccccc gaacgctctg caccttctga cgcagcctga | 1260 |
| gaatgacctg ccctggcccc agccctactc tgtgtaatag aataaaggcc tgcgtgtgtc | 1320 |
| tgtgttgagc gtgcgtctgt gtgtgcctgt gtgcgagtct gagtcagaga tttggagatg | 1380 |
| tctctgtgtg tttgtgtgta tctgtgggtc tccatcctcc atgggggctc agccaggtgc | 1440 |
| tgtgacaccc cccttctgaa tgaagccttc tgacctgggc tggcactgct gggggtgagg | 1500 |
| acacattgcc ccatgagaca gtcccagaac acggcagctg ctggctgtga caatggtttc | 1560 |
| accatcctta gaccaaggga tgggacctga tgacctggga ggactctctt agttcttacc | 1620 |
| ttttgtggtt ctcaataaaa cagaacttaa aaaattaaaa aaaaaaaaaa aaaaaaaaa | 1680 |

<210> SEQ ID NO 4
<211> LENGTH: 1260
<212> TYPE: DNA
<213> ORGANISM: Mus musculus

<400> SEQUENCE: 4

| | |
|---|---|
| ggcacgagca ggcggggagc aagaaagggg caggtacagc tgggcacggg gatcgtgcag | 60 |
| ctggtagctg gggcacgggc cccagctctg gctctggggc gagcaccttt ccagagccaa | 120 |
| cactgctctc aactcagtcc agcaagagag gggagccatc cagcccccgaa aggatacggc | 180 |
| tgcctactgc cgggcggatc ccaggctgga gcccgcttgg tcccataccc ctgctgccac | 240 |
| tctgtctcga ggggctgcag tgcagcaggg cctgtggcag gtgctctgca gatggaagca | 300 |
| gacgccttga gcccggtggg gctgggcctc ctgctgctgc ccttcttggt cacgctcctg | 360 |
| gctgccctgt gcgtgcgctg ccgtgagttg ccagtctcct atgacagcac ttccacagag | 420 |
| agtttgtacc caagaagcat cctcatcaag ccacctcaaa taaccgtccc ccgaacacct | 480 |
| gctgtttcct accctctagt cacttccttc ccacccctga ggcagccaga cctgctcccc | 540 |
| atcccgagat ccccacagcc ccttgggggt tccatcggga tgccatcttc ccagcagaat | 600 |
| tcagatgatg ccaacagtgt ggcaagctac gagaaccagg agccagcctg taagaatgtg | 660 |
| gatgcagatg aggatgaaga cgactatccc aacggctacc tagtggtgct gcctgacagt | 720 |
| agtcctgctg ccgtcccctgt tgtctcctct gctcctgtgc ctagcaaccc tgaccttgga | 780 |
| gacagtgcct tctctgtgga gtcgtgtgaa gattacgtga atgttcctga gagtgaggag | 840 |
| agcgcagagg cgtctctgga tgggagccgg gagtatgtga atgtgtcccc agagcagcag | 900 |
| ccagtgacca gggctgagct ggcctctgtg aactcccagg aggtggaaga cgaaggagaa | 960 |

```
gaggaagggg tggatggaga ggaagctccc gactatgaga atctacagga gcttaactga    1020
aagcctactg cagctgtctg tcctgaaact ggacttgctg gggtgtcgct aagaggatcc    1080
catttgatct ctgccttgcc acagcctgag aatcttcccc taacttattg tcactttggg    1140
gtccagtctg tgtccccaat attctgtacc ttctgataaa gcctgagaat gaatctggtt    1200
ccagccagac catgtcatgg aataaaggcc atgtgacata aaaaaaaaaa aaaaaaaaa     1260
```

<210> SEQ ID NO 5
<211> LENGTH: 19
<212> TYPE: RNA
<213> ORGANISM: Artificial
<220> FEATURE:
<223> OTHER INFORMATION: synthetic

<400> SEQUENCE: 5
gcacauccuc agauaguuu                                                  19

<210> SEQ ID NO 6
<211> LENGTH: 19
<212> TYPE: RNA
<213> ORGANISM: artificial
<220> FEATURE:
<223> OTHER INFORMATION: synthetic

<400> SEQUENCE: 6
caaacggccu cacacgguu                                                  19

<210> SEQ ID NO 7
<211> LENGTH: 19
<212> TYPE: RNA
<213> ORGANISM: artificial
<220> FEATURE:
<223> OTHER INFORMATION: synthetic

<400> SEQUENCE: 7
ggacgacuau cacaaccca                                                  19

<210> SEQ ID NO 8
<211> LENGTH: 19
<212> TYPE: RNA
<213> ORGANISM: Artificial
<220> FEATURE:
<223> OTHER INFORMATION: synthetic

<400> SEQUENCE: 8
ccaacagugu ggcgagcua                                                  19

<210> SEQ ID NO 9
<211> LENGTH: 19
<212> TYPE: RNA
<213> ORGANISM: Artificial
<220> FEATURE:
<223> OTHER INFORMATION: synthetic

<400> SEQUENCE: 9
cguguaggag ucuaucaaa                                                  19

<210> SEQ ID NO 10
<211> LENGTH: 30
<212> TYPE: DNA
<213> ORGANISM: artificial
<220> FEATURE:
<223> OTHER INFORMATION: synthetic

```
<400> SEQUENCE: 10
ggcagccggg agtatgtgaa tgtgtcccag                                              30

<210> SEQ ID NO 11
<211> LENGTH: 23
<212> TYPE: DNA
<213> ORGANISM: Artificial
<220> FEATURE:
<223> OTHER INFORMATION: synthetic

<400> SEQUENCE: 11
ggcgtcctgc ccttgctcca gcc                                                     23

<210> SEQ ID NO 12
<211> LENGTH: 30
<212> TYPE: DNA
<213> ORGANISM: Artificial
<220> FEATURE:
<223> OTHER INFORMATION: synthetic

<400> SEQUENCE: 12
gtggtgccca tcctggtcga gctggacggc                                              30

<210> SEQ ID NO 13
<211> LENGTH: 20
<212> TYPE: DNA
<213> ORGANISM: Artificial
<220> FEATURE:
<223> OTHER INFORMATION: synthetic

<400> SEQUENCE: 13
ccactggcat cgtgatggac                                                         20

<210> SEQ ID NO 14
<211> LENGTH: 20
<212> TYPE: DNA
<213> ORGANISM: Artificial
<220> FEATURE:
<223> OTHER INFORMATION: synthetic

<400> SEQUENCE: 14
gcggatgtcc acgtcacact                                                         20
```

LAT ADAPTER MOLECULE FOR ENHANCED T-CELL SIGNALING AND METHOD OF USE

STATEMENT OF RIGHTS TO INVENTIONS MADE UNDER FEDERALLY SPONSORED RESEARCH

This work was supported by the National Cancer Institute of the National Institutes of Health. The government has certain rights in the invention.

CROSS-REFERENCE TO RELATED APPLICATIONS

This application is a 35 U.S.C. §371 U.S. national entry of International Application PCT/US2010/033186 (WO 2010/129418) having an International filing date of Apr. 30, 2010, which claims priority to U.S. Provisional Patent Application Ser. No. 61/176,231, filed on May 7, 2009, both of which are incorporated herein in their entirety.

BACKGROUND

Immunotherapy for the treatment of cancer includes multiple basic strategies. Four particular immunotherapy approaches have garnered a significant amount of scientific attention and clinical interest. First is the use of general agents including cytokines such as interleukin-2 (IL-2) to stimulate the immune system of the patient. However, this method is limited by the toxicity of IL-2. Second is the use of vaccines to promote a specific immune response to a target antigen present on tumors, and preferably not present on normal cells. Antigens include whole cells, proteins, peptides or a wide variety of immunizing vectors. Such methods are under active investigation. Current studies have focused on improving response by adding additional factors to enhance the immune response. Third is the use of antibodies capable of binding various cell or tumor-specific antigens and coupled to various toxins. These reagents can, in certain settings, deplete cancer cells. Other antibody therapies are directed at targeting inhibitory molecule in T cells, which might be inhibiting a T cell response to a cancer. Fourth, some have used T cells expressing an appropriate T-cell receptor that binds to the specific target antigen to promote an immune response, known as adoptive cell therapy (ACT). This approach involves the identification ex vivo of autologous or allogeneic lymphocytes with anti-tumor activity which are then infused into cancer patients, often along with appropriate growth factors to stimulate their survival and expansion in vivo.

ACT has substantial theoretical and practical advantages over the approaches discussed above. It is necessary to identify only a small number of anti-tumor cells with the appropriate properties that can then be expanded to large numbers ex vivo for treatment. Alternatively, by identifying T-cell receptors (TCRs) that bind to the tumor antigens, expression constructs can be inserted into T-cells from the patient to be treated. In vitro tests can identify the exact populations and effector functions required for cancer regression, which can then be selected for expansion. Similar strategies can be used for the treatment of viral infection, particularly chronic viral infection, by identifying TCRs that bind viral antigens (e.g., from Epstein Barr virus, herpes virus, human immunodeficiency virus). Such therapies can be used in conjunction with more traditional therapies.

ACT has been highly successful in the treatment of melanoma. Patients with metastatic melanoma have a median survival of about 8 months with a two year survival rate of about 10-15% with the two approved treatments from the FDA, IL-2 and dacarbazine. Using transfer of autologous tumor-infiltrating lymphocytes (TIL) after lymphodepleting chemotherapy resulted in objective responses in 51% of 35 heavily pretreated patients with metastatic melanoma. (Dudley M E, et al. Cancer regression and autoimmunity in patients following clonal repopulation with anti-tumor lymphocytes. *Science* 2002; 298:850-854; Dudley M E, et al. Adoptive cell transfer therapy following non-myeloablative but lymphodepleting chemotherapy for the treatment of patients with refractory metastatic melanoma. *J. Clin. Oncol* 2005; 23:2346-2357). Further studies have confirmed the efficacy of the method of treatment of metastatic melanoma, particularly with myeloablating and lymphodepleting methods (Dudley, M E et al., Adoptive cell therapy for patients with metastatic melanoma: Evaluation of intensive myeloablative chemoradiation preparative regimens, *J. Clin. Oncol.* 2008; 5233-5239).

Treatment of melanoma using ACT has been successful at least in part due to the ability to identify autologous T-cells that react with MART-1 (Melanoma Antigen Recognized by T cells), and the subsequent cloning of T-cell receptors (TCR) that bind to MART-1. However, identification of T-cells having a high avidity for the desired antigen has proven to be a challenge as many of the tumor antigens are expressed during development or in one or more tissues in the body. Therefore, the T-cells expressing the appropriate TCR were likely deleted during clonal selection. Methods for cloning of TCRs for binding specific antigens have been established (see, e.g., Dossett. M L et al., Adoptive immunotherapy of disseminated leukemia with TCR-transduced, CD8+ T cells expressing a known endogenous TCR. *Mol. Ther.* 2009; 17:742-749). Such methods can include the cloning of an appropriate TCR from a non-human species, followed by alanine scanning, and subsequent mutational analysis to identify a TCR with higher affinity or efficacy that could be transduced into a T-cell for use in ACT (Parkhurst, M. R. et al., Characterization of genetically modified T-cell receptors that recognize the CEA: 691-699 peptide in the context of HLA-A2.1 on human colorectal cancer cells. *Clin. Cancer Res.* 2009; 15:169-180). However, even after administration of T-cells expressing TCRs with high avidity for their target antigen, such cells can become inhibited or inactivated for reasons that are not presently understood.

SUMMARY OF THE INVENTION

The invention provides compositions and methods to increase persistence of signaling in T-cells.

The invention provides isolated, non-naturally occurring linker for activation of T cells (LAT) polypeptides including at least an effective fragment of a full-length mammalian LAT 1 having at least one mutation at one amino acid capable of being ubiquitylated. For example, the invention provides at least an effective fragment of a full-length human LAT 1 polypeptide (SEQ ID NO: 1) having at least one amino acid substitution at amino acid 52 or amino acid 204, or both; or at least an effective fragment of a full-length mouse LAT 1 polypeptide (SEQ ID NO: 2) comprising at least one amino acid substitution at amino acid 53 or amino acid 121, or both. In certain embodiments of the invention, the amino acid substitution comprises a substitution of lysine with arginine. The invention further provides nucleic acid sequences encoding the polypeptide sequences of the invention.

The invention further provides an isolated cell or population of cells including an isolated, non-naturally occurring LAT polypeptide including at least an effective fragment of a full-length mammalian LAT 1 having at least one mutation at one amino acid capable of being ubiquitylated. In certain embodiments of the invention, the cell includes a T-cell receptor expressed on the surface of the cell, and capable of interacting with a specific target antigen, including a known specific target antigen. Specific target antigens include, but are not limited to, tumor antigens, viral antigens, and parasitic antigens. In certain embodiments, the T-cell receptor has a known amino acid sequence. In certain embodiments, the T-cell receptor is natively expressed by the cell. In certain embodiments, the T-cell receptor is expressed heterologously in the cell. In certain embodiments, the cell is a T-cell or a peripheral blood lymphocyte. In certain embodiments, the cell further includes a reporter construct to detect signaling through the T-cell receptor. For example, the cell can include a reporter gene operably linked to a promoter responsive to signaling through a T-cell receptor such as a jun promoter, an NFAT promoter, or an NF-kappa B promoter.

The invention also provides a mammal including LAT polypeptides having at least an effective fragment of a full-length mammalian LAT 1 having at least one mutation at one amino acid capable of being ubiquitylated. In certain embodiments, the LAT polypeptide is present in an isolated mammalian cell in the animal. In certain embodiments, the LAT polypeptide is provided to the mammalian cell by treating a cell from the mammal ex vivo with an expression construct to express the LAT polypeptide. In certain embodiments, the LAT polypeptide is provided in a cell from a syngeneic mammal by treating a cell from the syngeneic mammal ex vivo with an expression construct to express the LAT polypeptide. In certain embodiments, the mammal is a transgenic mammal. In certain embodiments the mammal is a mouse.

The invention provides methods of increasing signaling in response to an agonist in T-cell receptor including expressing a LAT polypeptide including at least an effective fragment of a full-length mammalian LAT 1 having at least one mutation at one amino acid capable of being ubiquitylated in the cell; and contacting the cell with a T-cell receptor agonist whereby T-cell receptor signaling is increased in the cell expressing a LAT polypeptide having at least one mutation at one amino acid capable of being ubiquitylated relative to a cell not expressing a LAT polypeptide having at least one mutation at one amino acid capable of being ubiquitylated. In certain embodiments, the method further includes detecting an increase in T-cell receptor signaling. Methods of detecting an increase in T-cell receptor signaling include, but are not limited to, detecting at least one of an increase in calcium flux, an increase in Ras signaling, an increase in activation of protein tyrosine kinase, an increase in T-cell proliferation, a decrease in T-cell apoptosis, expression of a reporter gene operably linked to a promoter sequence selected from the group consisting of jun, NFAT and NF-KB; CD25 and CD69 surface expression, and IL-2 production. In an embodiment, the enhanced signaling in response to an agonist in T-cell receptor is used to increase the effectiveness of Adoptive Cell Therapy (ACT).

The invention provides methods of improving the effectiveness of ACT by increasing signaling in T cells by the use of at least an effective fragment of a full-length mammalian LAT 1 having at least one mutation at one amino acid capable of being ubiquitylated. In an embodiment, the effectiveness of ACT is enhanced for the treatment of cancer. In an embodiment, the effectiveness of ACT is enhanced for the treatment of a viral infection. In an embodiment, the effectiveness of ACT is enhanced for the treatment of parasitic infection.

The invention provides methods of identifying a T-cell receptor for specific binding to a known target antigen by providing a cell expressing a T-cell receptor and a LAT polypeptide having at least one mutation at one amino acid capable of being ubiquitylated; contacting the cell with a specific target antigen in a context recognized by a T-cell receptor; and detecting signaling through the T-cell receptor wherein signaling through the T-cell receptor is indicative of the T-cell receptor binding the specific target antigen. Methods of detecting an increase in T-cell receptor signaling include, but are not limited to, detecting at least one of an increase in calcium flux, an increase in Ras signaling, an increase in activation of protein tyrosine kinase, an increase in T-cell proliferation, a decrease in T-cell apoptosis, expression of a reporter gene operably linked to a promoter sequence selected from the group consisting of jun, NFAT and NF-KB; CD25 and CD69 surface expression, and IL-2 production.

The invention provides methods for characterizing a subject suspected of suffering from or suffering from a defect in T-cell signaling, including providing a sample from a subject suspected of suffering from or suffering from a defect in T-cell signaling; detecting a mutation in LAT wherein the mutation alters ubiquitylation of LAT; whereby identification of a mutation in LAT that alters ubiquitylation of LAT characterizes the subject having a defect in T-cell signaling. In certain embodiments, the mutation comprises a mutation at one or more amino acids of human LAT at amino acid 52 or amino acid 204. In certain embodiments, the mutation of an amino acid includes a point mutation of the amino acid or a deletion of the amino acid. In certain embodiments, the mutation in LAT is detected by a method comprising a functional assay.

The invention provides isolated, non-naturally occurring double stranded RNA oligonucleotide duplex comprising from about 19 to about 24 nucleotides connected by covalent linkages, wherein one strand of the oligonucleotide duplex comprises a nucleobase sequence specifically hybridizable with nucleotides GCACAUCCUCAGAUAGUUU (SEQ ID NO: 5) which targets nucleotides 113-131 (from +1 at the ATG); CAAACGGCCUCACACGGUU (SEQ ID NO: 6) which targets nucleotides 153-171; GGACGACUAUCACAACCCA (SEQ ID NO: 7) which targets nucleotides 372-390; CCAACAGUGUGGCGAGCUA (SEQ ID NO: 8) which targets nucleotides 311-329 and CGUGUAGGAGUCUAUCAAA (SEQ ID NO: 9) which targets the antisense strand of nucleotides 311-329. Such compositions include a first strand having a sequence of GCACAUCCUCAGAUAGUUU (SEQ ID NO: 5); CAAACGGCCUCACACGGUU (SEQ ID NO: 6); GGACGACUAUCACAACCCA (SEQ ID NO: 7); CCAACAGUGUGGCGAGCUA (SEQ ID NO: 8); or CGUGUAGGAGUCUAUCAAA (SEQ ID NO: 9); and a second strand of RNA complementary thereto. In certain embodiments, the double stranded RNA oligonucleotide duplex is a siRNA or a shRNA. When the double stranded oligonucleotide is a siRNA, one or preferably both strands further include an AA nucleotide sequence on the 3' end. In certain embodiments, the isolated, non-naturally occurring double stranded RNA oligonucleotide duplex is present in a cell.

The invention provides kits including any of the compositions of the invention, or compositions for practicing any methods of the invention in appropriate packaging and/or with instructions for use.

DEFINITIONS

An "agent" is understood herein to include a therapeutically active compound or a potentially therapeutic active compound. An agent can be a previously known or unknown compound. As used herein, an agent is typically a non-cell based compound, however, an agent can include a biological therapeutic agent, e.g., peptide or nucleic acid therapeutic, cytokine, antibody, etc.

An "agonist" is understood herein as a chemical substance capable of initiating the same reaction or activity typically produced by the binding of an endogenous substance or ligand (e.g., antigen) to its receptor (e.g., TCR). An "antagonist" is understood herein as a chemical substance capable of inhibiting the reaction or activity typically produced by the binding of an endogenous substance (e.g., an endogenous agonist) to its receptor to prevent signaling through a receptor or to prevent downstream signaling that is the normal result of activation of the receptor. The antagonist can bind directly to the receptor or can act through other proteins or factors required for signaling. Agonists and antagonists can modulate some or all of the activities of the endogenous substance or ligand that binds to the receptor. Antagonists are typically characterized by determining the amount of the antagonist is required to inhibit the activity of the endogenous agonist. For example, an inhibitor at 0.01-, 0.1-, 1-, 5-, 10-, 50-, 100-, 200-, 500-, or 1000-fold molar concentration relative to the agonist can inhibit the activity of the agonist by at least 10%, 50%, 90%, or more. T-cell receptor agonists include CD3.

As used herein "amelioration" or "treatment" is understood as meaning to lessen or decrease at least one sign, symptom, indication, or effect of a specific disease or condition. For example, amelioration or treatment of cancer can be determined using the standard RECIST (Response Evaluation Criteria in Solid Tumors) criteria including the assessment of tumor burden, by survival time, reduced presence of tumor markers (e.g., prostate specific antigen), or any other clinically acceptable indicators of disease state or progression. Amelioration or treatment of a viral or parasitic infection can be determined by viral or parasite load, or secondary symptoms of the infection which vary with the particular pathogen. Amelioration and treatment can require the administration of more than one dose of an agent or therapeutic. Amelioration and treatment can include the prevention of a recurrence of cancer at the same site or a remote site. As used herein, "prevention" is understood as to limit, reduce the rate or degree of onset, or inhibit the development of at least one sign or symptom of a disease or condition. For example, a subject having a genetic predisposition to develop a disease may develop disease later in life, e.g., delay of BRCA1 or BRCA2 related breast cancer development from third or fourth decade of life to fifth or beyond. Prevention can include reducing the incidence in a population of infection with a specific pathogen, or delaying infection in an individual repeatedly exposed to the particular pathogen. Prevention can require the administration of more than one dose of an agent or therapeutic.

A "cell based therapeutic" as used herein is understood as a composition including a live cell for prevention, amelioration, or treatment of a disease or disorder. The cell can be from the subject to be treated or from a heterologous subject. The cell can be manipulated ex vivo after obtaining the cell from the source, and prior to administration of the cell to the subject for use as a therapeutic. Manipulations can include, but are not limited to, cell sorting, culturing, treatment with cytokines or growth factors, and transfection.

"Contacting a cell" is understood herein as providing an agent or isolated cell (e.g., T-cell expressing a selected TCR) to a test cell or cell to be treated in culture or in an animal, such that the agent or isolated cell can interact with the surface of the test cell or cell to be treated, potentially be taken up by the test cell or cell to be treated, and have an effect on the test cell or cell to be treated. The agent or isolated cell can be delivered to the cell directly (e.g., by addition of the agent to culture medium or by injection into the cell or tissue of interest), or by delivery to the organism by an enteral or parenteral route of administration for delivery to the cell by circulation, lymphatic, or other means.

As used herein, "changed as compared to a control" sample or subject is understood as having a level of the analyte or diagnostic or therapeutic indicator to be detected at a level that is statistically different than a sample from a normal, untreated, or control sample. Control samples include, for example, cells in culture, one or more laboratory test animals, or one or more human subjects. Methods to select and test control samples are within the ability of those in the art. An analyte can be a naturally occurring substance that is characteristically expressed or produced by the cell or organism (e.g., PSA) or a substance produced by a reporter construct (e.g, β-galactosidase or luciferase). Depending on the method used for detection the amount and measurement of the change can vary. For example, a change in the amount of cleavage of analyte present will depend on the exact reaction conditions and the amount of time after exposure to the agent the sample is collected. Changed as compared to a control reference sample can also include decreased binding of a ligand to a receptor in the presence of an antagonist or other inhibitor. Determination of statistical significance is within the ability of those skilled in the art.

As used herein "characterizing a subject suspected of comprising or comprising a defect in T-cell signaling" is understood as the process of obtaining a sample from a subject having or suspected of having a defect or other alteration in T-cell signaling as demonstrated, for example, by the detection of an autoimmune disorder or an immunodeficiency disorder, particularly when the disorder is of an unknown etiology, and analyzing the sample for an alteration of the sequence of LAT protein, particularly at a ubiquitylation site, or the expression level of LAT protein.

As used herein, "detecting", "detection" and the like are understood that an assay performed for identification of a specific analyte in a sample or a product from a reporter construct in a sample. Detection can also include identification of activation of a kinase or other enzyme, or a change in calcium channel gating by the detection of a calcium flux. Detection can include the identification of a mutation in a gene sequence, such as a point mutation, a deletion of all or part of the coding sequence or transcriptional/translational regulatory sequences of the gene, a truncation of the gene sequence, or any other alteration that can alter the expression level or the sequence of the protein expressed by the gene, particularly when the alteration of the sequence results in a phenotypic change in the subject. The amount of analyte detected in the sample can be none or below the level of detection of the assay or method.

As used herein, a "diagnostic marker" is understood as one or more signs or symptoms of a disease or condition that can be assessed, preferably quantitatively to monitor the progress or efficacy of a disease treatment or prophylactic treatment or method. A diagnostic marker can be a substance that is released by a tumor (e.g., antigens such as PSA or enzymes). A diagnostic marker can be tumor size. A diagnostic marker can be a change in blood counts or cellular function measured in an in vitro assay, or the presence and characteristics of metastases (number and size).

As used herein, the terms "effective" and "effectiveness" includes both pharmacological effectiveness and physiological safety. Pharmacological effectiveness refers to the ability of the treatment to result in a desired biological effect in the patient. Physiological safety refers to the level of toxicity, or other adverse physiological effects at the cellular, organ and/or organism level (often referred to as side-effects) resulting from administration of the treatment. On the other hand, the term "ineffective" indicates that a treatment does not provide sufficient pharmacological effect to be therapeutically useful, even in the absence of deleterious effects, at least in the unstratified population. (Such a treatment may be ineffective in a subgroup that can be identified by the expression profile or profiles.) "Less effective" means that the treatment results in a therapeutically significant lower level of pharmacological effectiveness and/or a therapeutically greater level of adverse physiological effects, e.g., greater liver toxicity.

Thus, in connection with the administration of a drug, a drug which is "effective against" a disease or condition indicates that administration in a clinically appropriate manner results in a beneficial effect for at least a statistically significant fraction of patients, such as a improvement of symptoms, a cure, a reduction in disease signs or symptoms, extension of life, improvement in quality of life, or other effect generally recognized as positive by medical doctors familiar with treating the particular type of disease or condition.

"Expression construct" as used herein is understood as a nucleic acid sequence including a sequence for expression as a polypeptide or nucleic acid (e.g., siRNA, shRNA) operably linked to a promoter and other essential regulatory sequences to allow for the expression of the polypeptide in at least one cell type. In a preferred embodiment, the promoter and other regulatory sequences are selected based on the cell type in which the expression construct is to be used. Selection of promoter and other regulatory sequences for protein expression are well known to those of skill in the art. An expression construction preferably also includes sequences to allow for the replication of the expression construct, e.g., plasmid sequences, viral sequences, etc. For example, expression constructs can be incorporated into replication competent or replication deficient viral vectors including, but not limited to, adenoviral (Ad) vectors, adeno-associated viral (AAV) vectors of all serotypes, self-complementary AAV vectors, and self-complementary AAV vectors with hybrid serotypes, self-complementary AAV vectors with hybrid serotypes and altered amino acid sequences in the capsid that provide enhanced transduction efficiency, lentiviral vectors, retroviral vectors, or plasmids for bacterial expression.

As used herein, "heterologous" as in "heterologous protein" is understood as a protein not natively expressed in the cell in which it is expressed. The heterologous protein may be, but need not be, from a different species. For example, during development, recombination and selection occurs in T-cells such that each T-cell expresses a single native TCR. A heterologous TCR can be expressed in a T-cell that expresses a different native TCR, a peripheral blood lymphocyte that does not express a TCR, or a cell in culture (e.g., a Jurkat cell) that does not express the specific TCR being expressed.

As used herein, "isolated" or "purified" when used in reference to a polypeptide means that a naturally occurring polypeptide or protein has been removed from its normal physiological environment (e.g., protein isolated from plasma or tissue) or is synthesized in a non-natural environment (e.g., artificially synthesized chemically or in a heterologous system). Thus, an "isolated" or "purified" polypeptide can be in a cell-free solution or placed in a different cellular environment (e.g., expressed in a heterologous cell type). The term "purified" does not imply that the polypeptide is the only polypeptide present, but that it is essentially free (about 90-95%, up to 99-100% pure) of cellular or organismal material naturally associated with it, and thus is distinguished from naturally occurring polypeptide. Similarly, an isolated nucleic acid is removed from its normal physiological environment. "Isolated" when used in reference to a cell means the cell is in culture (i.e., not in an animal), either cell culture or organ culture, of a primary cell or cell line. Cells can be isolated from a normal animal, a transgenic animal, an animal having spontaneously occurring genetic changes, and/or an animal having a genetic and/or induced disease or condition. Isolated cells can be further modified to include nucleic acids for the expression of heterologous T-cell receptors and/or wild-type or modified LAT proteins; reporter constructs; or be treated with various stimuli to modulate expression of a gene of interest.

As used herein, "kits" are understood to contain at least the non-standard laboratory reagents for use in the methods of the invention, such as cDNAs or nucleic acid constructs encoding wild-type or modified LAT proteins for the use in the methods of the invention. The invention can further include TCRs and the corresponding antigen or antigens, or non-specific T-cell agonists such as CD3. One or more cells or cell lines expressing LAT proteins with or without reporter constructs can be included in the kit. Constructs or cDNAs to express one or more TCRs can also be included. The kit can further include any other components required to practice the method of the invention, as dry powders, concentrated solutions, or ready to use solutions. In some embodiments, the kit comprises one or more containers that contain reagents for use in the methods of the invention; such containers can be boxes, ampules, bottles, vials, tubes, bags, pouches, blister-packs, or other suitable container forms known in the art. Such containers can be made of plastic, glass, laminated paper, metal foil, or other materials suitable for holding reagents.

As used herein, a "LAT polypeptide" is understood a sequence of contiguous amino acids of a sequence provided by at least one of GenBank No. NP_001014987 (*Homo sapien*, SEQ ID NO: 1), XP_001147360.1 (*Pan troglodytes*), XP_001102058.1 (*Macaca mulatto*), XP_001502393.1 (*Equus caballus*), NP_110480 (*Rattus norvegicus*), NP_034819 (*Mus musculus*, SEQ ID NO: 2), XP_849910.1 (*Canis familiaris*), and NP_001098448 (*Bos taurus*), in the version available on the day of filing of the instant application, having a length of at least 50 amino acids, at least 60 amino acids, at least 70 amino acids, at least 80 amino acids, at least 90 amino acids, at least 100 amino acids, at least 125 amino acids, at least 150 amino acids, at least 175 amino acids, at least 200 amino acids, at least 210 amino acids, or at least 220 amino acids. In an embodiment, a LAT polypeptide further includes one or more amino acid deletions or substitutions such that the LAT polypeptide is at least 80% identical, 85% identical, 90% identical, 95% identical, 97% identical, 98% identical, 99% identical to at least 50 amino acids, at least 60 amino acids, at least 70 amino acids, at least 80 amino acids, at least 90 amino acids, at least 100 amino acids, at least 125 amino acids, at least 150 amino acids, at least 175 amino acids, at least 200 amino acids, at least 210 amino acids, or at least 220 amino acids of an amino acid sequence provided by one of the GenBank numbers set forth above. Mutations can be conservative mutations, or non-conservative mutations. Conservative mutations replace an amino acid with an amino acid having similar structural and/or chemical properties. Amino acids are typically grouped based on the properties of their side chains. For example, Lysine, arginine, and histidine are basic amino acids. Aspartic acid and glutamic acid have acidic side chains. Glycine, alanine, valine, leucine, isoleucine, proline, phenylalanine, methionine, tryptophan, and cysteine have non-polar side chains. Asparagine, glutamine, serine, threonine, and tyrosine have uncharged side chains.

A LAT polypeptide can be encoded a native nucleic acid sequence such as those provided by GenBank numbers NM_001014987 (*Homo sapien*, SEQ ID NO: 3), XM_001147360 (*Pan troglodytes*), XM_001502343.1 (*Equus caballus*), NM_030853.1 (*Rattus norvegicus*), NM_010689 (*Mus musculus*, SEQ ID NO: 4), XM_844817.1 (*Canis familiaris*), and NM_001104978.1 (*Bos taurus*). Alternatively, a LAT polypeptide can be encoded by any nucleotide sequence that provides a polypeptide having the sequence of a LAT polypeptide. The degeneracy of the genetic code is well understood such that the native nucleic acid sequence can be substantially modified without altering the sequence of the amino acid encoded. LAT polypeptide sequences and LAT nucleic acid sequences are provided, for example in U.S. Pat. No. 7,118,889 which is incorporated herein by reference. An active fragment of a LAT polypeptide includes a truncated, mutated, or full length version of the LAT protein from any species wherein the active fragment of LAT can support signaling through a T-cell receptor as determined using any of the methods provided in the Examples below, for example by a calcium flux assay, a kinase assay, or a reporter construct assay in a T cell that does not express and endogenous LAT (e.g., JCam 2.5 cells) at a statistically significant level over background in a cell not expressing any active fragment of LAT. In an embodiment, an active fragment of LAT can support signaling through a T cell receptor at a level of at least 10% of that supported by a wild-type LAT polypeptide using any of the methods provided in the Examples below.

The term "label" or "detectable label" as used herein refers to any atom or molecule which can be used to provide a detectable (preferably quantifiable) signal, and which can be attached to a nucleic acid or protein. Labels may provide signals detectable by fluorescence, radioactivity, colorimetry, gravimetry, X-ray diffraction or absorption, magnetism, enzymatic activity, and the like. Various methods of labeling polypeptides and glycoproteins are known in the art and may be used. Examples of labels for polypeptides include, but are not limited to, the following: radioisotopes (e.g., $^3$H), fluorescent labels (e.g., FITC, rhodamine, lanthanide phosphors), enzymatic labels (e.g., horseradish peroxidase, beta-galactosidase, luciferase, alkaline phosphatase), biotinyl groups, predetermined polypeptide epitopes recognized by a secondary reporter (e.g., leucine zipper pair sequences, binding sites for secondary antibodies, metal binding domains, epitope tags). In some embodiments, labels are attached by spacer arms of various lengths to reduce potential steric hindrance. In others, the label is part of the fusion protein, e.g. Green Fluorescent Protein (GFP), Yellow Fluorescent Protein (YFP).

A "non-naturally occurring" polypeptide sequence or nucleic acid sequence and the like is an amino acid or nucleotide sequence that is not present in the proteome or the genome, respectively, of the organism from which the sequence is derived. In certain embodiments, the amino acid or nucleotide sequence can include one or more mutations that have not been identified as naturally occurring mutations. In certain embodiments, the amino acid or nucleotide sequence can be a truncated sequence or a sequence with one or more internal deletions. In certain embodiments, the amino acid or nucleotide sequence can be fused to another amino acid or nucleotide sequence, e.g., a coding sequence, a regulatory sequence, etc., that confers a new property to the sequence not present in the naturally occurring sequence. A non-naturally occurring polypeptide sequence or nucleic acid sequence can include one or more non-naturally occurring amino acids or nucleic acids.

"Obtaining" is understood herein as manufacturing, purchasing, or otherwise coming into possession of.

As used herein, "oligonucleotide sequence" is understood as a non-coding nucleic acid sequence prepared by chemical synthesis methods or by transcription from a construct including an appropriate promoter sequence. A double stranded RNA oligonucleotide sequence as used herein includes a single strand forming a hairpin structure (e.g., shRNA) or joined by other non-nucleic acid linkages, or two separate strands annealed to form a double stranded structure.

A "parasitic antigen" as used herein is any protein or nucleic acid, or fragment thereof, from a parasite that can infect a subject, in the context of the invention, preferably an mammalian subject, and preferably on the surface of the cell to allow the antigen to be recognized by a TCR.

The phrase "pharmaceutically acceptable carrier" is art recognized and includes a pharmaceutically acceptable material, composition or vehicle, suitable for administering compounds of the present invention to mammals. The carriers include liquid or solid filler, diluent, excipient, solvent or encapsulating material, involved in carrying or transporting the subject agent from one organ, or portion of the body, to another organ, or portion of the body. Each carrier must be "acceptable" in the sense of being compatible with the other ingredients of the formulation and not injurious to the patient. For example, pharmaceutically acceptable carriers for administration of cells typically is a carrier acceptable for delivery by injection, and do not include agents such as detergents or other compounds that could damage the cells to be delivered. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, α-tocopherol, and the like; and metal chelating agents, such as citric acid, ethylenediamine tetraacetic acid (EDTA), sorbitol, tartaric acid, phosphoric acid, and the like.

Formulations of the present invention include those suitable for oral, nasal, topical, transdermal, buccal, sublingual, intramuscular, intravenous, intraarterial, intraperotineal, rectal, vaginal and/or various parenteral administration routes. The formulations may conveniently be presented in unit dosage form and may be prepared by any methods well known in the art of pharmacy. The amount of active ingredient that can be combined with a carrier material to produce a single dosage form will generally be that amount of the compound that produces a therapeutic effect.

As used herein, "plurality" is understood to mean more than one. For example, a plurality refers to at least two, three, four, five, or more.

A "polypeptide" or "peptide" as used herein is understood as two or more independently selected natural or non-natural amino acids joined by a covalent bond (e.g., a peptide bond). A peptide can include 2, 3, 4, 5, 6, 7, 8, 9, 10, 11, 12, 13, 14, 15, 16, 17, 18, 19, 20, or more natural or non-natural amino acids joined by peptide bonds. Polypeptides as described herein include full length proteins (e.g., fully processed proteins) as well as shorter amino acids sequences (e.g., fragments of naturally occurring proteins or synthetic polypeptide fragments).

"Reporter construct" as used herein is understood to be an exogenously inserted gene, often present on a plasmid, with a detectable gene product, under the control of a promoter sequence. The activity of the promoter is modulated upon signaling through the TCR pathway. A plasmid containing the c-jun promoter upstream of a reporter can be transfected into T-cell cell line, e.g., Jurkat cells, CCRF-CEM cells, CML-T1 cells. Preferably, the gene product is easily detectable using a quantitative method. Common reporter genes include luciferase and beta-galactosidase. The reporter construct can be transiently inserted into the cell by transfection or infection methods. Alternatively, stable cell lines can be made using methods well known to those skilled in the art, or cells can be obtained from transgenic animals expressing a reporter construct. The specific reporter gene or method of detection is not a limitation of the invention.

"RNA interference" refers to a target directed disruption of expression from a particular RNA transcript using a double stranded RNA molecule, either a siRNA or a shRNA. "siRNA" refers to a small interfering RNA, sometimes known as short interfering RNA or silencing RNA, is a class of 20-25 nucleotide-long double-stranded RNA molecules involved in the RNA interference (RNAi) pathway, where it interferes with the expression of a specific gene. SiRNAs have a well-defined structure: a short (usually 21-nt) double strand of RNA (dsRNA) with 2-nt 3' overhangs on either end. However, siRNAs can vary in length from about 19 to about 24 nucleotides in length. Each strand has a 5' phosphate group and a 3' hydroxyl (—OH) group. Structures of siRNAs and methods for design are provided, for example in WO02/44321, incorporated herein by reference. As used herein, "small hairpin RNA" or "short hairpin RNA" (shRNA) is a sequence of RNA that makes a tight hairpin turn that can be used to silence gene. A shRNA is composed of a single-stranded RNA with two self-complementary regions that allow the RNA to fold back upon itself and form a stem-loop structure with an intramolecular duplex region and an unpaired loop region.

A "sample" as used herein refers to a biological material that is isolated from its environment (e.g., blood or tissue from an animal, cells, or conditioned media from tissue culture) and is suspected of containing, or known to contain an analyte, such as a tumor cell or a product from a reporter construct. A sample can also be a partially purified fraction of a tissue or bodily fluid. A reference sample can be a "normal" sample, from a donor not having the disease or condition, or from a normal tissue in a subject having the disease or condition (e.g., normal tissue vs. tumor tissue). A reference sample can also be from an untreated donor or cell culture not treated with an active agent (e.g., no treatment or administration of vehicle only) and/or stimulus. A reference sample can also be taken at a "zero time point" prior to contacting the cell or subject with the agent or cell to be tested.

"Small molecule" as used herein is understood as a compound, typically an organic compound, having a molecular weight of no more than about 1500 Da, 1000 Da, 750 Da, or 500 Da. In an embodiment, a small molecule does not include a polypeptide or nucleic acid.

A TCR "specifically binds" a target antigen when the target antigen is bound with at least 100-fold, preferably at least 500-fold, preferably at least 1000-fold preference as compared to a non-specific antigen or a pool of non-specific antigens, and wherein specific binding of the target antigen to the TCR promotes signaling through the TCR. Preference for binding of a specific antigen can be determined, for example, by use of cellular assays such as for proliferation, cytokine production or cytolytic activity on specific targets. More rigorously one can perform binding assays of particular TCRs on appropriate peptide-MHC complexes. The antigen can be a self-antigen or a non-self antigen.

A "subject" as used herein refers to living organisms. In certain embodiments, the living organism is an animal. In certain preferred embodiments, the subject is a mammal. In certain embodiments, the subject is a domesticated mammal. Examples of subjects include humans, non-human primates, monkeys, dogs, cats, mice, rats, cows, horses, goats, and sheep. A human subject may also be referred to as a patient.

A subject "suffering from or suspected of suffering from" a specific disease, condition, or syndrome has a sufficient number of risk factors or presents with a sufficient number or combination of signs or symptoms of the disease, condition, or syndrome such that a competent individual would diagnose or suspect that the subject was suffering from the disease, condition, or syndrome. Methods for identification of subjects suffering from or suspected of suffering from conditions such as cancer, or viral or parasitic infection is within the ability of those in the art. Subjects suffering from, and suspected of suffering from, a specific disease, condition, or syndrome are not necessarily two distinct groups.

As used herein, "T-cell receptor" or "TCR" is a molecule found on the surface of T lymphocytes (or T cells). TCRs recognize antigens in the context of a major histocompatibility complex (MHC) molecule present on the surface of an antigen presenting cell, or in the context of cell surface expression (e.g., expressed on a tumor cell or a virally infected cell). A T-cell receptor is a heterodimer consisting of antigen-MHC binding, clonotypic alpha and beta chains in about 95% of T cells, and consisting of gamma and delta chains in about 5% of T-cells. The CD3- and ζ-chains, together with the alpha and beta TCR chains, form what is known as the T cell receptor. Engagement of the TCR with antigen and MHC results in activation of its T lymphocyte through a series of biochemical events mediated by associated enzymes, co-receptors, and accessory molecules, including LAT.

As used herein, "T-cell receptor signaling" as used herein is understood as a series of inter-related events initiated by the binding of either a non-specific (e.g., anti-CD3 antibody) or a specific (antigen presented by an MHC) ligand to a TCR and resulting in a number of responses by the cell in which the TCR is expressed. When the TCR expressed in a T-cell is activated the responses include kinase activation including activation of Lck and/or Fyn and ZAP-70 protein tyrosine kinases, activation of the serine protein kinase, protein kinase C, intracellular calcium flux, translocation of transcription factors to the nucleus including c-jun and NFAT, cytoskeletal remodeling due to activation of Rac and CDC42, cell proliferation, phosphoinositide (PI) turnover, decreased apoptosis, CD69 expression, secretion of cytokines such as IL-2 and in the case of cytolytic T cells, lysis of appropriate target cells.

"Target antigen" is understood as any peptide, nucleic acid, hapten, or other small molecule to which a TCR can specifically bind. The peptide or nucleic acid can be a protein fragment or a nucleic acid fragment from the subject or a pathogenic agent (e.g., virus, parasite). The fragment can be a naturally occurring fragment, e.g., a fragment of a processed protein presented in an MHC by an antigen presenting cell, or a peptide selected for potential antigenic properties, target specificity, or other desired properties.

"Therapeutically effective amount," as used herein refers to an amount of an agent which is effective, upon single or multiple dose administration to the cell or subject, in prolonging the survivability of the patient with such a disorder beyond that expected in the absence of such treatment.

An agent can be administered to a subject, either alone or in combination with one or more therapeutic agents, as a pharmaceutical composition in mixture with conventional excipient, e.g., pharmaceutically acceptable carrier, or therapeutic treatments such as radiation.

The pharmaceutical agents may be conveniently administered in unit dosage form and may be prepared by any of the methods well known in the pharmaceutical arts, e.g., as described in *Remington's Pharmaceutical Sciences* (Mack Pub. Co., Easton, Pa., 1980). Formulations for parenteral administration may contain as common excipients such as sterile water or saline, polyalkylene glycols such as polyethylene glycol, oils of vegetable origin, hydrogenated naphthalenes and the like. In particular, biocompatible, biodegradable lactide polymer, lactide/glycolide copolymer, or polyoxyethylene-polyoxypropylene copolymers may be useful excipients to control the release of certain agents.

It will be appreciated that the actual preferred amounts of active compounds used in a given therapy will vary according to e.g., the specific compound being utilized, the particular composition formulated, the mode of administration and characteristics of the subject, e.g., the species, sex, weight, general health and age of the subject. Optimal administration rates for a given protocol of administration can be readily ascertained by those skilled in the art using conventional dosage determination tests conducted with regard to the foregoing guidelines.

The nucleic acids for expression of the peptides of the invention can, for example, be administered ex vivo, with a dosage ranging from about 0.001 µg to about 1000 µg, depending upon various factors including the number of cells to which the constructs should be delivered. effective dosages would range from about 1 µg to about 100 µg, that is about 10 µg to about 50 µg, about 0.1 µg to about 10 µg, about 1 µg to about 20 µg, or any range bracketed by any of the two values listed, for an adult liver. Dosages can be adjusted for the size of the plasmid or viral vector to be delivered. It is understood that if the nucleic acid is to be delivered systemically, higher doses will be used.

For administration of viral particles ex vivo, dosages are typically provided by number of virus particles (or viral genomes) and effective dosages would range from about $1 \times 10^{10}$ to $1 \times 10^{14}$ particles, about $1 \times 10^{10}$ to $1 \times 10^{13}$ particles, about $1 \times 10^{11}$ to $1 \times 10^{14}$ particles, about $1 \times 10^{12}$ to $1 \times 10^{14}$ particles, or about $1 \times 10^{9}$ to $1 \times 10^{15}$ particles delivered to the T cells. The effective dose can be the number of particles when different expression construct to be delivered when different expression constructs encoding different genes are administered separately. In alternative embodiment, the effective dose can be the total number of particles administered, of one or more types. The methods herein contemplate administration of an effective amount of compound or compound composition to achieve the desired or stated effect. It is understood that if the nucleic acid is to be delivered systemically, higher doses will be used.

The term "transfection" as used herein refers to the introduction of a transgene into a cell. The term "transgene" as used herein refers to any nucleic acid sequence which is introduced into the genome of a cell by experimental manipulations. Transfection may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, biolistics (i.e., particle bombardment) and the like.

The term "stable transfection" or "stably transfected" refers to the introduction and integration of a transgene into the genome of the transfected cell. The term "stable transfectant" refers to a cell which has stably integrated one or more transgenes into the genomic DNA.

The term "transient transfection" or "transiently transfected" refers to the introduction of one or more transgenes into a transfected cell in the absence of integration of the transgene into the host cell's genome. The term "transient transfectant" refers to a cell which has transiently integrated one or more transgenes.

"Tumor antigen" as used herein can be any antigen expressed exclusively or preferentially in tumor cells, including, but not limited to, MART-1, gp100, carcinoembryonic antigen (CEA; CEACAM5; CD66e), cancer-testis antigen (NY-ESO-1), alphafetoprotein (AFP), CA-125 (cancer antigen-125, MUC-16), mucin 1 (MUC-1), epithelial tumor antigen (ETA), tyrosinase, and melanoma-associated antigen (MAGE).

A "viral antigen" as used herein is any protein or nucleic acid, or fragment thereof from a virus that can infect a cell, in the context of the invention, preferably a mammalian cell, and preferably on the surface of the cell bound to the MHC molecule to allow the antigen to be recognized by a TCR. As used herein, viral antigens are preferably from viruses that produce chronic or sustained infections including, but not limited to, herpes viruses, human immunodeficiency viruses, and hepatitis viruses.

The term "wild-type" or "WT" refers to a gene or gene product which has the characteristics of that gene or gene product when isolated from a naturally occurring source. A wild-type gene is that which is most frequently observed in a population and is thus arbitrarily designated the "normal" or "wild-type" form of the gene. In contrast, the term "modified" or "mutant" refers to a gene or gene product which displays modifications (e.g. deletions, substitutions, etc.) in sequence and or functional properties (i.e., altered characteristics) when compared to the wild-type gene or gene product. It is noted that naturally-occurring mutants can be isolated; these are identified by the fact that they have altered characteristics when compared to the wild-type gene or gene product.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

Unless specifically stated or obvious from context, as used herein, the term "or" is understood to be inclusive.

Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

All oligonucleotide sequences are written from the 5'-end to the 3'-end unless otherwise specifically noted.

Nucleic acids encoding the various polypeptide sequences can readily be determined by one of skill in the art, and any sequence encoding any of the polypeptide sequences of the invention falls within the scope of the invention, as well as the complement of the coding sequence, and double stranded nucleic acid sequences including coding sequences and their complement as well as artificial and non-naturally occurring sequences and their complement.

Any compositions or methods provided herein can be combined with one or more of any of the other compositions and methods provided herein.

BRIEF DESCRIPTION OF THE FIGURES

FIGS. 9A to 9C show calcium fluxes in response to CD3 stimulation in cells transfected with siRNA targeted to LAT (A) or a construct simultaneously expressing an shRNA targeted to LAT and GFP (B and C).

DETAILED DESCRIPTION

Figure 1:
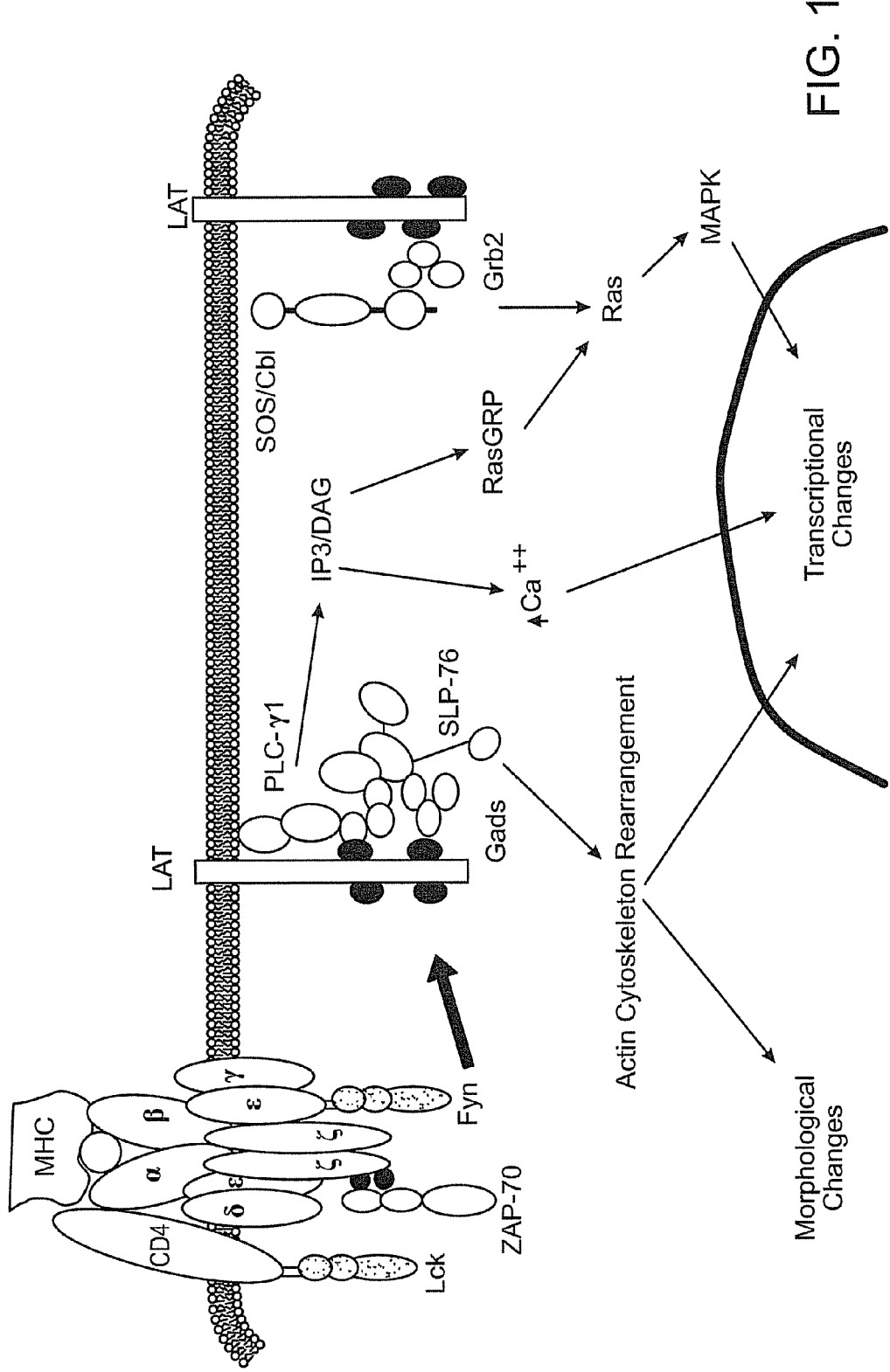
FIG. 1: Simplified schematic of proximal signaling in a T-cell.

The engagement of the multi-subunit T-cell receptor (TCR) is rapidly followed by the activation of protein tyrosine kinases (PTKs) that phosphorylate a number of downstream substrates, of which a prominent example is LAT, a transmembrane adapter protein. Phosphorylated tyrosines on LAT serve as docking sites for multiple proteins containing Src homology 2 domains, including adapters such as Gads and Grb2, which in turn are associated with other signaling proteins. For example, SLP-76 is recruited to LAT through association with Gads. The LAT-Gads-SLP-76 complex creates a platform for the recruitment of numerous other signaling molecules, including phospholipase C-γ1 (PLC-γ1), the Rho family GTPase exchange factor Vav, and the ubiquitin ligase Cb1. Thus, TCR engagement induces the formation of LAT-based signaling complexes that initiate intracellular signals required for T-cell activation.

To ensure an appropriate immune response to antigenic challenge, without generating an autoimmune response, it is crucial that T-cell activation be tightly regulated. TCR engagement activates several mechanisms that have been described to attenuate TCR-mediated signaling, including ligand-induced internalization and degradation of activated signaling molecules. For example, c-Cb1 mediated ubiquitin conjugation to the TCR chain has been correlated with TCR internalization into endosomal compartments and the subsequent degradation of the receptor in activated T cells. In addition, Cb1 proteins downregulate PTKs such as Lck, Fyn, and ZAP-70, as well as non-PTK molecules such as the p85 subunit of phosphatidylinositol 3-kinase and the guanine nucleotide exchange factor Vav.

This tightly controlled, short lived response is advantageous during an endogenous immune response, however, when T-cells are administered for a chronic disease such as cancer or a viral infection, persistence of T-cells and a T-cell response is advantageous.

As demonstrated herein, expression of an ubiquitin-deficient LAT in T-cells results in increased signaling through the T-cell receptor as compared to a cell expressing wild-type LAT. This increased signaling could result in an increase in T-cell viability by increased cell proliferation or decreased or delayed apoptosis, increased cytokine release, or in the case of cytotoxic T cells, enhanced lytic activity on appropriate targets. Increased signaling through the TCR could also allow for the use of TCRs having a lower avidity for the target antigen.

While most studies on internalization as a means of signal downregulation in T cells have focused on the fate of the TCR, results from studies tracking individual components of TCR-induced microclusters in real time suggest that the fates of the TCR and signaling proteins diverge during T-cell activation. In systems using either stimulatory antibodies or lipid bilayers to model T-cell activation, whereas microclusters contain both the TCR and signaling molecules initially, signaling molecules dissociate from the receptor soon thereafter. Upon TCR activation, LAT-containing signaling clusters are internalized into various distinct intracellular compartments prior to dissipating rapidly. Expression of versions of c-Cb1 defective in the RING finger domain, which mediates ubiquitin ligase activity, resulted in severely decreased internalization of LAT and SLP-76 clusters, decreased ubiquitylation of LAT, and an increase in basal LAT levels, as well as elevated basal and TCR-induced phosphorylated LAT (pLAT) levels. The inhibition of LAT internalization was also observed in T cells from mice lacking c-Cb1. These data are consistent with a model in which TCR-mediated activation first leads to the rapid formation of signaling complexes, after which c-Cb1 activity is involved in the internalization and possible downregulation of a subset of activated signaling molecules. Given the essential scaffolding role of the adapter protein LAT in T-cell activation, the regulated internalization of activated LAT signaling complexes may be one efficient strategy by which to control the duration and localization of signaling from microclusters and, thus, regulate the kinetics, intensity, and specificity of T-cell signaling.

To further analyze the role of LAT ubiquitylation in TCR signaling, lysines identified as potential ubiquitylation sites in LAT were mutated (K52R, K204R and 2KR which contains both lysine mutations) and the ability of LAT to act as a substrate for ubiquitylation was assayed in tissue culture cells. Using the immunoprecipitation-western blot methods described below in the Examples, it was determined that LAT was ubiquitylated primarily on amino acid K52 (see, e.g., FIG. 2B). As expected, the 2KR LAT construct in which both K52 and K204 are mutated to arginines also showed severely decreased ubiquitylation. Ubiquitylation sites in mouse are at amino acids 53 and 121.

It is expected that mutation at the equivalent amino acids in mouse would have the same effect on T cell signaling in mouse cells as the mutations in human cells. Further, it is expected that mutation of the lysines to any amino acid that could not be ubiquitylated, i.e., any amino acid other than cysteine, that did not disrupt protein folding would have a similar effect on T cell signaling. Preferably, the substitution is a conservative substitution, wherein the basic lysine amino acid is replaced with another basic amino acid, i.e., arginine or histidine. The K to R substitution is prevents ubiquitination because the alpha-carboxyl group of the terminal glycine on ubiquitin forms an isopeptide bond with an (epsilon) amino group in the side chain of a lysine residue of the target protein. Thus K is mutated to R to preserve the basic residue which may be important for protein structure, but this substitution prevents ubiquitylation. Generation of coding sequence for proteins including point mutations is well within the ability of those of skill in the art (see, e.g., Alberts et al., Molecular Biology of the Cell, 2$^{nd}$ Edition, c. 1989, Garland Publishing Inc.). Moreover, methods of testing such proteins for activity using any of the methods provided herein is routine and well within the ability of those of skill in the art.

Using the 2KR LAT mutant, time to formation and internalization of LAT containing clusters was determined using established methods (see Balagopalan et al., c-Cb1-mediated regulation of LAT-nucleated signaling in complexes. *Mol. Cell. Bio.* 2007; 27:8622-8636, incorporated herein by reference). Briefly, T-cells expressing fluorescently tagged proteins, e.g., LAT-YFP (yellow fluorescent protein) were dropped onto an antibody-coated coverslip maintained in media at 37° C. Receptor-initiated signaling is triggered by the settling of the cells on the coverslip surface. Images were captured using high resolution microscopy.

Figure 3:
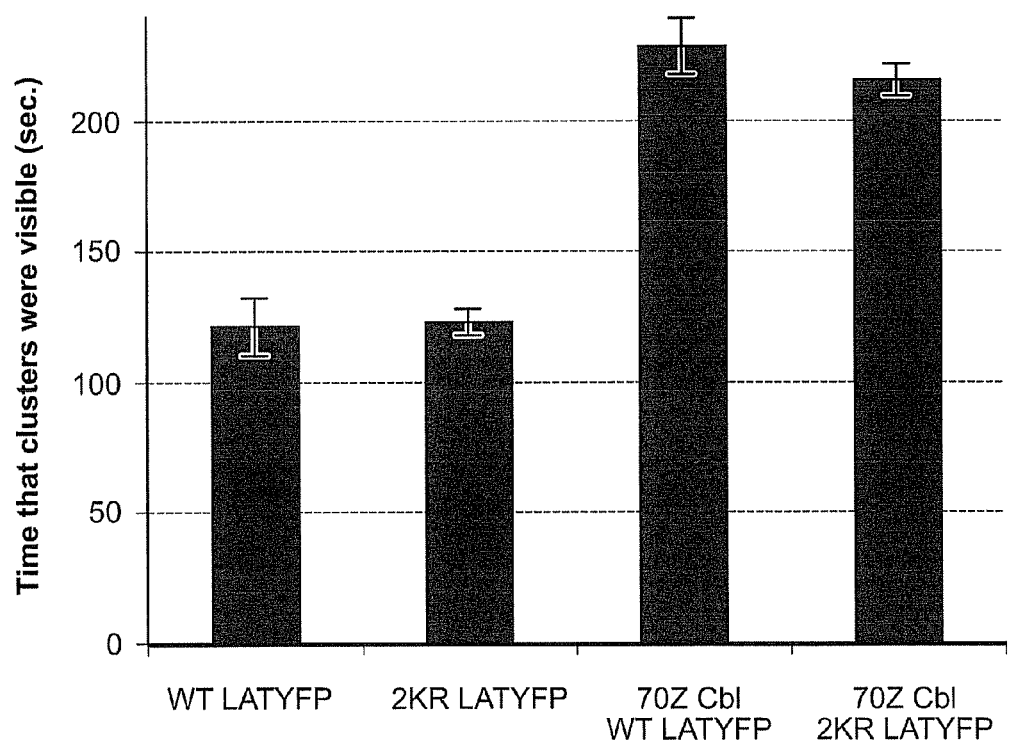
FIG. 3: Graph of the time that LAT containing clusters persisted in cells after TCR stimulation in cells expressing wild-type LAT, mutant 2KR LAT, or cells co-expressing 70ZCb1 with wild-type or mutant 2KR LAT.

The results from an experiment using cells expressing either wild-type LAT-YFP or the 2KR LAT-YFP either alone or in conjunction with 70Z Cb1, a ubiquitin deficient Cb1 mutant, are shown in FIG. 3. Expression of the wild-type or mutant LAT-YFP had no effect on the amount of time that LAT containing clusters could be observed in the cells. This is in contrast to cells expressing a 70Z Cb1 in conjunction with each of the LAT-YFPs in which LAT containing clusters were demonstrated to be visible for about twice as long. These data indicate that the variation in persistence of LAT containing clusters in response to stimulation of the TCR is not dependent upon ubiquitylation of LAT.

However, 2KR LAT-YFP was found to be more stable in cells than wild-type LAT-YFP (see FIG. 4). Jurkat E6.1 cells transfected with expression constructs encoding either mutant or wild-type LAT-YFP were sorted to provide populations with equivalent LAT-YFP levels. Cells were cultured for 24 hours and then total YFP was analyzed. Cells expressing the 2KR mutant LAT were found to have significantly higher mean YFP levels. These results demonstrate that LAT lacking ubiquitylation sites is more stable than wild-type LAT.

To test whether higher protein levels of 2KR LAT-YFP reflected increased transcription of this construct, transcript levels were measured by quantitative RT-PCR. Jurkat E6.1 cells were transiently transfected with wild-type LAT-YFP or 2KR LAT-YFP and were evaluated for chimeric LAT-YFP and endogenous LAT-YFP transcript expression. Transcript levels of the □-actin gene were used as a reference. Transcript levels of wild-type LAT-YFP and 2KR LAT-YFP were not significantly different.

Figure 5A:
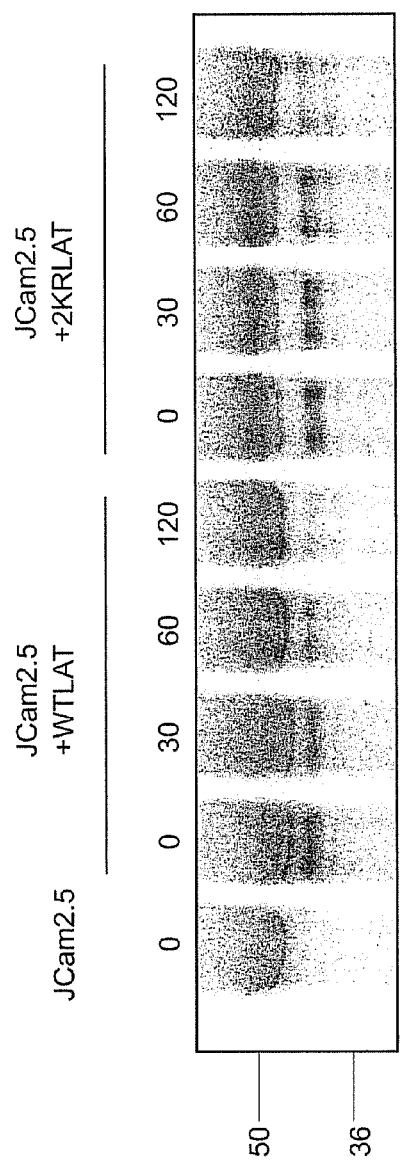
FIG. 5: (A) an autoradiograph of LAT protein lifetime in Jurkat JCam2.5 cells expressing a wild-type or mutated version (2KRLAT) of LAT is resistant to ubiquitylation. (B) Quantification of autoradiographs show in A. (C) Pulse chase analysis of cells treated with proteasomal inhibitor MG-132, the lysosomal inhibitor leupeptin or a combination of the two. (D) Quantification of the autoradiographs shown in C. (E) Mean YFP levels in cells expressing wild-type or 2KR LAT-YFP incubated with proteasomal inhibitor MG-132.

The rate of degradation of wild-type and 2KR-LAT proteins were assayed by pulse chase analysis (FIGS. 5A and B). Jurkat JCam2.5 cells that do not express endogenous LAT were stably transfected with expression constructs encoding either 2KR mutant or wild-type LAT. Cells were incubated or "pulsed" with $S^{35}$ labeled methionine and cysteine. Whole cell lysates were prepared at various time-points after the initial pulse and LAT immunoprecipitations were performed. Autoradiograph analysis revealed that the half-life of 2KR LAT was found to be greater than 120 minutes, whereas the half-life of wild-type LAT was found to be 70 minutes. The availability of more LAT for longer periods of time suggests a method to provide increased and/or prolonged signaling in T cells. Treatment of cells with the proteosome inhibitor MG-132 also inhibited degradation of LAT, but no inhibition was observed as a result of treatment of cells with the lysosome protease inhibitor leupeptin (FIG. 5 C-E), further demonstrating that LAT degradation was ubiquitin and proteosome mediated.

To determine if the persistence of the non-ubiquitylated LAT did in fact correspond to an increase in persistence of LAT signaling, Jurkat JCam2.5 cells lacking endogenous LAT (FIG. 6) were transfected with expression constructs encoding either 2KR mutant or wild-type LAT. Cells were stimulated with CD3 antibody and calcium influx was monitored using a fluorescent dye. The level and persistence of T-cell signaling was increased in the cells transfected with the 2KR LAT relative to cells expressing only wild-type LAT. No signaling was detected in cells not expressing LAT.

Discuss New FIG. 7 BIT

To further confirm an increase in TCR signaling in cells expressing the 2KR-LAT, Jurkat JCam2.5 cells transfected with expression constructs encoding either 2KR mutant or wild-type LAT were stimulated with CD3 and assayed for production of CD69, the earliest identified inducible cell surface glycoproteins as a way to measure T-cell activation through another signaling pathway (FIG. 6C). Expression of CD69 was comparable in unstimulated cells expressing either wild-type or 2KR LAT, however, after stimulation with CD3, expression of CD69 was substantially higher in cells expressing 2KR LAT. These results further demonstrate an increase in TCR signaling in cells expressing a ubiquitin deficient LAT.

To further elucidate the role of LAT ubiquitylation in T cell signaling, endogenous LAT expression was knocked-down in Jurkat E6.1 cells and wild-type or 2KR LAT-YFP were re-expressed in these cells. Western blotting experiments revealed that endogenous LAT expression was dramatically reduced in cells transfected with LAT-targeting siRNA. Furthermore, 2KR LAT-YFP was expressed at higher levels than wild-type LAT-YFP as expected (from results in FIG. 4). TCR-induced signaling outputs such as Ca++ influx, NFAT activation and CD69 upregulation were elevated in cells reconstituted with 2KR LAT-YFP as compared with cells expressing wild-type LAT-YFP (FIG. 7). Importantly, comparison of signaling in cells expressing equivalent levels of wild-type and 2KR LAT-YFP revealed that 2KR LAT-YFP caused more effective T cell signaling on a per molecule basis as compared with wild-type LAT. Furthermore, the LAT ubiquitin mutant shifted the dose response, so that a lower stimulation was required to trigger a response of the same magnitude. This may be of benefit in physiological settings of limited ligand concentrations.

The effects of 2KR expression was tested in non-transformed primary human CD4+ T cells. Endogenous LAT expression was reduced using siRNA targeting LAT and simultaneously plasmids expressing wild-type LAT-YFP or 2KR LAT-YFP were re-expressed. Transfected cells were stimulated with various doses of CD3 and CD28 and evaluated for CD69 upregulation 16 hours post-stimulation. Consistent with results obtained in Jurkat cells, enhanced CD69 upregulation was observed in cells expressing 2KR LAT at all doses tested (FIG. 8). Taken together, these results demonstrate a critical role for LAT ubiquitylation in maintaining normal T cell signaling. In all cell types tested, cells bearing ubiquitin-deficient LAT were hyperresponsive to stimulation through the TCR.

Figure 9A:
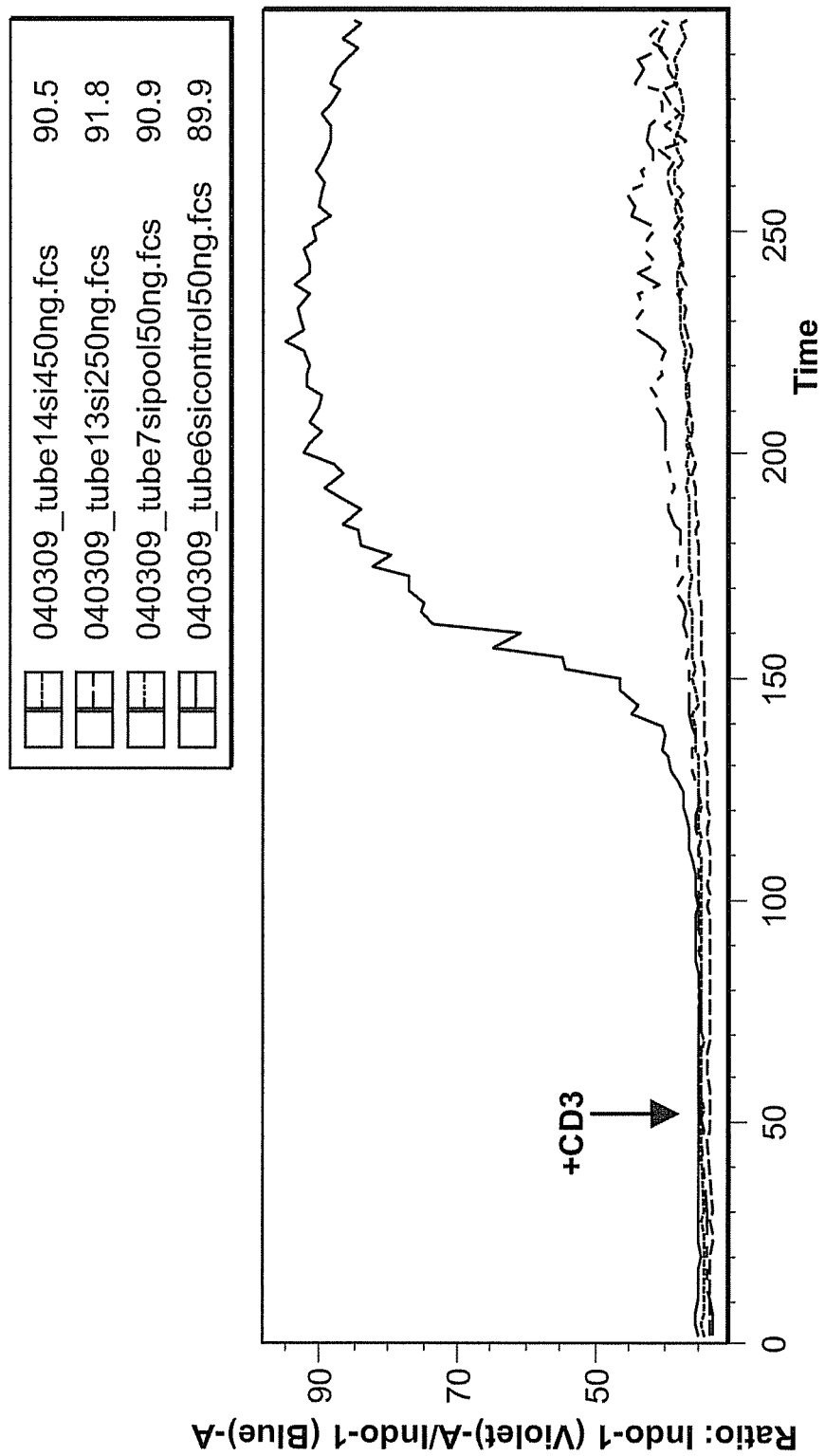

To further analyze the role of LAT expression in T-cell signaling, siRNAs and shRNAs targeted to LAT were designed and transfected into cells. Cells were tested for calcium influx in response to stimulation with CD3 antibody (FIG. 9). All three of the siRNAs targeted to LAT were able to decrease calcium flux to background level in cells (FIG. 9A). shRNA-GFP fusion constructs allowed for the gating of cells based on the expression of GFP in the cells, which presumably correlates with the level of shRNA present in the cell and inversely correlates with LAT protein levels. The greater the expression of GFP, the more substantial the dampening of the calcium influx into the cells in response to stimulation with CD3 (FIGS. 9B and C). These data demonstrate that LAT expression has a dose dependent effect on signaling through the TCR.

The 2KR LAT protein can be used as a therapeutic agent for the treatment of various diseases and conditions for which a temporally extended immune response, beyond that in cells expressing wild-type LAT is desired. The 2KR LAT protein can be expressed in cells expressing a TCR directed to the antigen of interest, e.g., a cancer antigen, or a pathogenic antigen, e.g., a viral antigen, a parasitic antigen, a bacterial antigen, etc. In certain embodiments of the invention, a nucleic acid sequence encoding the 2KR protein, or an effective fragment thereof, is delivered to the T cell, typically in conjunction with the TCR targeted to the antigen of interest. However, in certain embodiments, T cells expressing the TCR of interest can be selected and expanded.

In an exemplary method, T cells are collected from the subject to be treated and expanded ex vivo under conditions appropriate to allow re-administration of the cells to the subject after transfer of the desired coding sequences. Methods such as transfection by electroporation or transduction by adenoviral, adeno-associated viral, retroviral, or lentiviral systems; or other methods and systems that include the use of reagents acceptable for administration to humans are preferred.

In an alternative embodiment, a nucleic acid encoding a protein for administration can be administered systemically. Larger doses of nucleic acid would be used for administration systemically as compared to dosages for ex vivo administration. Such considerations are well understood by those of skill in the art.

In certain embodiments, cell specific promoters for expression of LAT proteins in T-cells would be used. Such promoters include, but are not limited to, human CD2, distal Lck, and proximal Lck. In other embodiments, non-tissue specific promoters such as non-tissue specific promoters including viral promoters such as cytomegalovirus (CMV) promoter, β-actin promoter including the chicken β-actin promoter, phosphoglycerate kinase (PGK) promoter, ubiquitin promoter including hybrid ubiquitin promoter, and EF-1α promoter can be used.

Other regulatory sequences for inclusion in expression constructs include poly-A signal sequences, for example SV40 polyA signal sequences. The inclusion of a splice site (i.e., exon flanked by two introns) has been demonstrated to be useful to increase gene expression of proteins from expression constructs.

Enhancers can also be used in the constructs of the invention. Enhancers include, but are not limited to enhancer is selected from the group consisting of cytomegalovirus (CMV) enhancer, an elongation factor 1-alpha enhancer, and liver-specific enhancers.

For viral sequences, the use of viral sequences including inverted terminal repeats, for example in AAV viral vectors can be useful. Certain viral genes can also be useful to assist the virus in evading the immune response after administration to the subject.

In certain embodiments of the invention, the viral vectors used are replication deficient, but contain some of the viral coding sequences to allow for replication of the virus in appropriate cell lines. The specific viral genes to be partially or fully deleted from the viral coding sequence is a matter of choice, as is the specific cell line in which the virus is propagated. Such considerations are well known to those of skill in the art.

Further, viruses with specific tropisms that will cause them to go to efficiently infect liver cells can be selected for use in the method of the invention. For example, the AAV8 serotype is known to be preferentially hepatotrophic (Nakai et al., 2005. J. Virol. 79:214-224).

Compositions and methods for gene delivery to various organs and cell types in the body are known to those of skill in the art. Such compositions and methods are provided, for example in U.S. Pat. Nos. 7,459,153; 7,282,199; 7,259,151; 7,041,284; 6,849,454; 6,410,011; 6,027,721; and 5,705,151, all of which are incorporated herein by reference. Expression constructs provided in the listed patents and any other known expression constructs for gene delivery can be used in the compositions and methods of the invention.

Methods of viral vector design and generation are well known to those of skill in the art, and methods of preparation of viral vectors can be performed by any of a number of companies or using routine laboratory methods. Expression constructs provided herein can be inserted into any of the exemplary viral vectors listed below.

Gene transfer and nucleic acid therapeutics have been demonstrated to typically be more effective when delivered to the desired site of action rather than systemically, e.g., by delivering the viral vector ex vivo, both increasing delivery and transduction efficiency and reducing undesirable systemic effects.

Gene transfer to the liver using AAV vectors for the treatment of hemophilia B is currently being tested in a phase 1 trial, see, e.g., clinicaltrials.gov identifier NCT00515710. The study includes intra-hepatic administration of AAV2-hFIX (Factor IX) and secondary outcomes for analysis include determining the potential efficacy in each dose group by measuring biological and physiological activity of the transgene product. This human trial follows a large number of animal experiments in which AAV vectors were efficiently delivered to the liver using AAV2 and AAV8 viral vectors (e.g., Mount et al. Blood. 2002; 99:2670-2676; Cardone et al., *Hum Mol Genet.* 2006; 15:1225-1236; Daly et al., *Gene Ther.* 2001; 8:1291-1298; McEachern et al. J Gene Med. 2006; 8:719-729; Koeberl et al., Gene Ther. 2006; 13:1281-1289; Moscioni et al., *Mol Ther.* 2006; 14:25-33; Park et al., *Exp Mol Med.* 2006; 38:652-661; Scallan et al. *Blood.* 2003; 102: 2031-2037; Seppen et al. *Mol Ther.* 2006; 13:1085-1092; each of which is incorporated by reference)

Many studies have demonstrated that local administration to the eye provides efficient transduction of cells with viral vectors. In the Bainbridge study (*NEJM,* 358:2231-2239, 2008, incorporated herein by reference), the tgAAG76 vector, a recombinant adeno-associated virus vector of serotype 2 was used for gene delivery. The vector contains the human RPE65 coding sequence driven by a 1400-bp fragment of the human RPE65 promoter and terminated by the bovine growth hormone polyadenylation site, as described elsewhere.

Additional AAV vectors are provided in the review by Rolling 2004 (*Gene Therapy* 11: 526-S32, incorporated herein by reference). Hybrid AAV viral vectors, including AAV 2/4 and AAV2/5 vectors are provided, for example, by U.S. Pat. No. 7,172,893 (incorporated herein by reference). Such hybrid virus particles include a parvovirus capsid and a nucleic acid having at least one adeno-associated virus (AAV) serotype 2 inverted terminal repeat packaged in the parvovirus capsid. However, the serotypes of the AAV capsid and said at least one of the AAV inverted terminal repeat are different. For example, a hybrid AAV2/5 virus in which a recombinant AAV2 genome (with AAV2 ITRs) is packaged within a AAV Type 5 capsid.

Self-complementary AAV (scAAV) vectors have been developed to circumvent rate-limiting second-strand synthesis in single-stranded AAV vector genomes and to facilitate robust transgene expression at a minimal dose (Yokoi, 2007. IOVS. 48:3324-3328, incorporated herein by reference). Self-complementary AAV-vectors were demonstrated to provide almost immediate and robust expression of the reporter gene inserted in the vector. Subretinal injection of $5\times10^8$ viral particles (vp) of scAAV.CMV-GFP resulted in green fluorescent protein (GFP) expression in almost all retinal pigment epithelial (RPE) cells within the area of the small detachment caused by the injection by 3 days and strong, diffuse expression by 7 days. Expression was strong in all retinal cell layers by days 14 and 28. In contrast, 3 days after subretinal injection of $5\times10^8$ vp of single stranded (ss)AAV.CMV-GFP, GFP expression was detectable in few RPE cells. Moreover, the ssAAV vector required 14 days for the attainment of expression levels comparable to those observed using scAAV at day 3. Expression in photoreceptors was not detectable until day 28 using the ssAAV vector. The use of the scAAV vector in the gene delivery methods of the invention can allow for prompt and robust expression from the expression construct. Moreover, the higher level of expression from the scAAV viral vectors can allow for delivery to of the viral particles intravitreally rather than subretinally.

Various recombinant AAV viral vectors have been designed including one or more mutations in capsid proteins or other viral proteins. It is understood that the use of such modified AAV viral vectors falls within the scope of the instant invention.

Kota et al. (Cell, 137: 1005-1017, 2009, incorporated herein by reference) demonstrated efficient delivery of an AAV expression vector containing an shRNA targeted to miR-26a in vivo in a model of rat hepatocellular carcinoma.

Adenoviral vectors have also been demonstrated to be useful for gene delivery. For example, Mori et al (2002. *IOVS,* 43:1610-1615, incorporated herein by reference) discloses the use of an adenoviral vector that is an E-1 deleted, partially E-3 deleted type 5 Ad in which the transgene (green fluorescent protein) is driven by a CMV promoter. Peak expression levels were demonstrated upon injection of $10^7$ to $10^8$ viral particles, with subretinal injection providing higher levels of expression than intravitreal injection.

Efficient non-viral ocular gene transfer was demonstrated by Farjo et al. (2006, PLoS 1:e38, incorporated herein by reference) who used compacted DNA nanoparticles as a system for non-viral gene transfer to ocular tissues. As a proof of concept, the pZEEGFP5.1 (5,147 bp) expression construct that encodes the enhanced green fluorescent protein (GFP) cDNA transcriptionally-controlled by the CMV immediate-early promoter and enhancer was used. DNA nanoparticles were formulated by mixing plasmid DNA with CK30PEG10K, a 30-mer lysine peptide with an N-terminal cysteine that is conjugated via a maleimide linkage to 10 kDa polyethylene glycol using known methods. Nanoparticles were concentrated up to 4 mg/ml of DNA in saline. The compacted DNA was delivered at a 0.6 µg dose to the vitreal cavity. GFP expression was observed in the lens, retina, and pigment epithelium/choroid/sclera by PCR and microscopy.

Further, a number of patents have been issued for methods of ocular gene transfer including, but not limited to, U.S. Pat. No. 7,144,870 which provides methods of hyaluronic acid mediated adenoviral transduction; U.S. Pat. Nos. 7,122,181 and 6,555,107 which provide lentiviral vectors and their use to mediate ocular gene delivery; U.S. Pat. No. 6,106,826 which provides herpes simplex viral vectors and their use to mediate ocular gene delivery; and U.S. Pat. No. 5,770,580 which provides DNA expression vectors and their use to mediate ocular gene delivery. Each of these patents is incorporated herein by reference.

Hepatic gene delivery has also been demonstrated in a number of studies. For example, self-complementary adeno-associated virus vectors containing a novel liver-specific human factor IX expression cassette were found to enable highly efficient transduction of murine and nonhuman primate liver (Nathwani et al., Blood. 2006 Apr. 1; 107:2653-61). An AAV-2 genome encoding the hfIX gene was cross-packaged into capsids of AAV types 1 to 6 using efficient, large-scale technology for particle production and purification. In immunocompetent mice, the resultant vector particles expressed high hFIX levels ranging from 36% (AAV-4) to more than 2000% of normal (AAV-1, -2, and -6), which would exceed curative levels in patients with hemophilia. (Grimm et al., Blood. 2003 Oct. 1; 102:2412-9).

Further, a number of patents have been issued for methods of hepatic gene or nucleic acid transfer including, but not limited to U.S. Pat. Nos. 7,615,537 and 7,351,813 which provide methods for expression of clotting factor in the liver; U.S. Pat. No. 7,528,118 which provides methods for delivery of siRNA to liver to reduce expression of ApoB; U.S. Pat. No. 7,498,017 provides a cationic poly cyclic imidazolinium-containing compound for condensing nucleic acid for delivery to a cell, including a liver cell; and U.S. Pat. No. 6,967,018 for delivery of AAV-1, 2, or 5 vectors for the expression of adiponectin. Each of these patents related to hepatic gene or nucleic acid transfer is incorporated herein by reference.

Such viral vectors and methods can be used for the delivery of nucleic acids encoding modified LAT proteins to T cells.

Self-Complementary Adenoviral Vectors

Under normal circumstances, AAV packages a single-stranded DNA molecule of up to 4800 nucleotides in length. Following infection of cells by the virus, the intrinsic molecular machinery of the cell is required for conversion of single-stranded DNA into double stranded form. The double-stranded form is then capable of being transcribed, thereby allowing expression of the delivered gene to commence. It has been shown in a number of cell and tissue types that second strand synthesis of DNA by the host cell is the rate-limiting step in expression. By virtue of already being packaged as a double stranded DNA molecule, self-complementary AAV (scAAV) bypasses this step, thereby greatly reducing the time to onset of gene expression.

Self-complementary AAV is generated through the use of vector plasmid with a mutation in one of the terminal resolution sequences of the AAV virus. This mutation leads to the packaging of a self-complementary, double-stranded DNA molecule covalently linked at one end. Vector genomes are required to be approximately half genome size (2.4 KB) in order to package effectively in the normal AAV capsid. Because of this size limitation, large promoters are unsuitable for use with scAAV. Most broad applications to date have used the cytomegalovirus immediate early promoter (CMV) alone for driving transgene expression. A long acting, ubiquitous promoter of small size is useful in a scAAV system.

Xu et al (Mol. Ther. 11: 523-530, 2005, incorporated herein by reference) have demonstrated efficient shRNA expression in mammalian cancer cells after delivery using an scAAV vector. U.S. Pat. No. 7,465,583 teaches delivery of nucleic acid to various cell types using scAAV vectors (incorporated herein by reference).

Gene Transfer Using Plasmid DNA

Delivery of plasmid DNA has been demonstrated to be an efficient method of gene transfer in vivo (Yoshino et al., 2006, and Budker et al, 1996; Zhang et al., 1997; each incorporated herein by reference). The methods provided herein include gene transfer ex vivo. In the methods, the nucleic acid is delivered directly to the tissue. Therefore, the nucleic acid need not be packaged or modified to direct it to the appropriate tissue. Moreover, as the nucleic acid is delivered to the cells over a short time period, the nucleic acid is far less susceptible to the effects of nucleases than a nucleic acid delivered systemically. The invention provides expression of a coding sequence in naked DNA which includes DNA not enclosed in a viral capsid, but can include other compounds to promote cellular uptake and/or to increase the stability of the DNA. Such compounds are preferably safe for use in humans and such considerations are well known to those of skill in the art. Typically, naked DNA is in the form of plasmid DNA, such as supercoiled plasmid DNA to provide some protection against nucleases that may be present. Gene transfer using plasmid DNA can also include the use of plasmid DNA that has been cut, for example, with a restriction enzyme, to provide a linear DNA molecule. Gene transfer using plasmid DNA may be beneficial as it may overcome the obstacle of immune response to viral capsid proteins.

Example 1

Materials and Methods

Reagents:

Human anti-CD3ϵ (UCHT or HIT3a) monoclonal antibodies were purchased from Pharmingen and were used to coat coverslips. The following antibodies were used for western blotting and immunoprecipitation: Anti-HA-HRP (Roche), mouse anti-LAT (Upstate), mouse anti-β actin (SIGMA), rabbit anti-pLAT191 (Invitrogen), mouse anti-pY clone 4G10 (Millipore). APC-conjugated CD69 antibody was from BD Pharmingen. Indo-1 AM was from Invitrogen. OKT3 binding the human CD3-ϵ chain was used to trigger T cell activation.

COS-7 Cell Transfection, Immunoprecipitation and Immunoblotting:

COS-7 cells were transfected using Lipofectamine® Plus reagent as recommended by the manufacturer (SIGMA®). Briefly, 60 mm dishes were seeded with cells and 70% confluent cell cultures were used for transfection. Cells were co-transfected with WT, K52, K204 or 2KR LAT (0.5 μg) and HA-Ub (0.5 μg). 24 hours post-transfection, cells were lysed in ice-cold Nonidet®-40 lysis buffer (50 mM Tris pH 7.4; 150 mM NaCl; 5 mM EDTA; 5 mM EGTA; 50 mM NaF; 1% NP-40), and cellular lysates were subjected to immunoprecipitation using mouse anti-LAT monoclonal antibody (Upstate). Protein A/G Plus-Agarose beads (Santa Cruz Biotechnology) were used for immunoprecipitation. Protein samples were resolved by sodium-dodecyl-sulfate polyacrylamide gel electrophoresis (SDS-PAGE), transferred to nitrocellulose membrane and immunoblotted with appropriate primary antibodies followed by enhanced chemiluminescence (Upstate).

Cell Culture and Transfection of Jurkat Cells:

Jurkat E6.1 cells and LAT-deficient, Jurkat cells have been described previously (Zhang et al., 2000, incorporated herein by reference). All Jurkat cells were cultured in RPMI 1640 supplemented with 10% fetal bovine serum and antibiotics. For protein expression, Jurkat cells were transfected with 5-25 μg plasmid DNA using the electroporation system, solution T, and program H-10 from LONZA. Transiently transfected cells were harvested or analyzed 24-48 hrs. post-transfection.

Confocal Microscopy and Image Processing to Calculate Lifetime of LAT Clusters:

Spreading assays were performed as described previously (Bunnell et al., 2002). Briefly chambered coverslips (LabTek) were coated overnight at 4° C. with the stimulatory antibody human anti-CD3ε (HIT3a or UCHT at 10 µg/ml). Jurkat E6.1 cells transfected with YFP- and CFP-tagged constructs were plated onto coated coverslips containing imaging buffer (RPMI 1640 without phenol red, 10% fetal calf serum, 20 mM Hepes). Movement of fluorescent proteins in live cells were observed with a Zeiss® Axiovert 200 microscope equipped with a Perkin-Elmer® Ultraview spinning disc confocal system (Perkin Elmer). Images were captured with an Orca-ERII CCD camera (Hamamatsu). A hot air blower and an objective warmer were used to maintain live samples at 37° C.

IPLab 3.6 (Scanalytics® Inc.) was used for most image processing. Movies were prepared from z-stacks by making a maximum intensity projection of a given time point and then making a sequence of all the projections. Kymographs were made from regions of interest (ROI) drawn around moving clusters of interest and the movement of clusters was analyzed using IPLab3.6. Graphs were prepared with Microsoft Excel (Microsoft®).

Pulse-Chase Analysis:

Jurkat Jcam2.5 cells reconstituted with wild-type or 2KR LAT ($1\times10^7$) were washed once with PBS and incubated for 30 min at 37° C. under 5% $CO_2$ in methionine-deficient RPMI 1640 medium (Sigma). The cells were pulse-labeled with [$^{35}$S]methionine-[$^{35}$S]cysteine mix (GE Healthcare®) for 20 min at 37° C. under 5% $CO_2$ and washed twice in PBS. Equal portions were added to 500 ml of RPMI-FBS for each time point of the chase period and incubated at 37° C. At the indicated time points, cells were harvested and lysed in ice-cold lysis buffer containing 1% Brij, 1% n-Octyl-D-glucoside, 50 mM Tris-HCl, pH 7.6, 150 mM NaCl, 5 mM ethylenediaminetetraacetic acid, 1 mM $Na_3VO_4$ and complete protease inhibitor tablets (Roche®). Protein A/G Plus-Agarose beads (Santa Cruz Biotechnology) were used for immunoprecipitation. Protein samples were resolved on sodium dodecyl sulfate-polyacrylamide gel electrophoresis (SDS-PAGE), transferred to nitrocellulose membrane, and placed on a phosphor imager for detection of labeled protein.

Measurement of $Ca^{++}$ Influx:

Cells were incubated with 5 µM Indo-1-AM (Molecular Probes®) and 0.5 mM probenecid (Sigma®) in RPMI 1640 medium at 37° C. for 45 min. The cells were washed with RPMI 1640, resuspended in imaging buffer containing 0.5 mM probenecid, and kept at room temperature for 30-45 min. The cells were incubated at 37° C. for 5 min before measurements, stimulated with 50 ng/ml OKT3 antibody and analyzed using the LSR II (BD Biosciences). The data were processed using Tree Star FlowJo® software.

siRNA and shRNA Mediated Depletion of LAT Levels:

The small interfering RNA (siRNA) corresponding to human LAT and the control nontargeting siRNA pool were purchased from Dharmacon Inc. The SMARTpool duplexes for human LAT were designed to target the following mRNA sequences: SMARTpool duplex 1, GCACAUCCUCAGAUAGUUU (SEQ ID NO: 5) which targets nucleotides 113-131 (from +1 at the ATG); duplex 2, CAAACGGCCUCACACGUU (SEQ ID NO: 6) which targets nucleotides 153-171; duplex 3, GGACGACUAUCACAACCCA (SEQ ID NO: 7) which targets nucleotides 372-390; and duplex 4, CCAACAGUGUGGCGAGCUA (SEQ ID NO: 8) which targets nucleotides 311-329. Briefly, Jurkat E6.1 cells were transfected with control siRNA or siRNA for LAT (100 µm/$5\times10^6$ cells) by using a LONZA® electroporator, solution T, and program H-10.pSUPER.neo.GFP was obtained from OligoEngine®.

The shRNA for LAT were designed to target the following mRNA sequences (sh1: CCAACAGUGUGGCGAGCUA (SEQ ID NO: 8) that corresponds to nucleotides 311-329 in the LAT coding sequence with ATG as +1, sh5: CGUGUAGGAGUCUAUCAAA (SEQ ID NO: 9) that corresponds to nucleotides 118-136 in LAT 5' UTR). Briefly, Jurkat E6.1 cells were transfected with control shRNA or shRNA for LAT (25 µg/$10\times10^6$ cells) by using a LONZA® electroporator, solution T, and program H-10. Cells were analyzed 48 hrs. post-transfection.

QPCR

Total RNA was prepared on transfected cells using Trizol (Invitrogen, Carlsbad, Calif.). For each sample, 1 µg RNA was reverse transcribed into cDNA with oligo d(T) and the AffinityScript™ QPCR cDNA Synthesis Kit (Agilent, Santa Clara, Calif.). For real-time, quantitative PCR, the same sense primer was used for both endogenous and transfected LAT: 5'GGCAGCCGGGAGTATGTGAATGTGTCCAG 3' (SEQ ID NO: 10). Endogenous LAT was detected by adding an antisense primer from the 3' UTR not present in the transfected construct: 5' GGCGTCCTGCCCTTGCTCCAGCC 3'(SEQ ID NO: 11). Transfected LAT was detected by adding an antisense primer from the YFP coding sequence: 5' GTGGTGCCCATCCTGGTCGAGCTGGACGGC 3' (SEQ ID NO: 12). The primers and cDNA were combined with Brilliant® II QRT-PCR AffinityScript Master Mix containing SYBR green (Agilent, Santa Clara, Calif.), and qper reactions were run and analyzed on the Mx3000P (Agilent, Santa Clara, Calif.). β-actin was used for normalization: Sense: 5' CCACTGGCATCGTGATGGAC 3' (SEQ ID NO: 13) Antisense: 5' GCGGATGTCCACGTCACACT 3' (SEQ ID NO: 14). Relative levels were quantitated using the DDCT method.

Flow Cytometry Assays:

E6.1 Jurkat cells were transfected with wild-type or 2KR LAT-YFP constructs. Twenty four hours following transfection cells were analyzed and sorted for similar levels of expression using a Beckton-Dickinson® FACS Vantage SE flow cytometer (Beckton-Dickinson® Inc.). Sorted cells were cultured for 24 hrs. and analyzed again for expression levels. The data were analyzed in Tree Star FlowJo® software. Mean LAT-YFP levels (+s.e.m.) were measured.

Functional Assays:

For measurement of $Ca^{++}$ influx, cells were incubated with 5 M Indo-1-AM (Molecular Probes®) and 0.5 mM probenecid (Sigma®) in RPMI 1640 medium at 37° C. for 45 min. The cells were washed with RPMI 1640, resuspended in imaging buffer containing 0.5 mM probenecid, and kept at room temperature for 30-45 min. The cells were incubated at 37° C. for 5 min before measurements, stimulated with various doses of soluble OKT3 antibody and analyzed using the LSR II (BD Biosciences). The data were processed using Tree Star FlowJo® software.

For measurement of surface CD69 levels in Jurkat E6.1 or JCam2.5 cells, $1\times10^6$ cells were stimulated in solution with various doses of CD3 (OKT3). Isolated CD4+ PBMCs were stimulated on various doses of platebound CD3 (OKT3) and CD28 in a 96 well round bottom plate. Sixteen hours post-stimulation, cells were stained with APC-conjugated CD69 (BD Pharmingen), and surface expression was analyzed on a FACSCalibur cytometer (BD Biosciences). The data were processed using Tree Star FlowJo software.

For luciferase assays, cells were simultaneously transfected with siRNA targeting LAT or control siRNA and YFP, LAT-YFP or 2KR LAT-YFP along with 4 µg of a NF-AT luciferase reporter plasmid and 1 µg/ml of a control β-galactosidase expression vector. 48 hours post-transfection, cells were stimulated with various dilutions of OKT3 in solution. After 6 h at 37° C., cells were washed with PBS and lysed in 50 µl reporter lysis buffer from the Luciferase assay system kit (Promega) and clarified by centrifugation. The supernatant was then analyzed in the reporter assay according to the manufacturer's protocol and read on an EG and G Berthold Microplate Luminometer LB96V (EG and G Berthold). For β-galactosidase activity, plates were read on Versamax microplate reader (Molecular Devices) 30 min after the addition of the relevant reagent. Luciferase activity was normalized to internal β-galactosidase controls.

siRNA Mediated Depletion of LAT Levels and Re-Expression of LAT:

The small interfering RNA (siRNA) corresponding to human LAT and the control nontargeting siRNA pool were purchased from Dharmacon Inc. The SMARTpool duplexes for human LAT were designed to target the following mRNA sequences: SMARTpool duplex 4, CCAACAGUGUGGC-GAGCUA (SEQ ID NO: 8) which targets nucleotides 311-329. Briefly, Jurkat E6.1 cells were transfected with control siRNA or siRNA for LAT (100 µm/5×106 cells) by using an LONZA® electroporator, solution T, and program H-10. Cells were analyzed 48 hrs. post-transfection. For re-expression LAT sequences corresponding to 311-329 were altered by site-directed mutagenesis to render re-expressed LAT resistant to targeting siRNA.

Primary human PBMCs culture and transfection PBMCs from healthy donors were isolated by Ficoll-Hypaque density gradient centrifugation. Human T helper cells (i.e. CD4+) were negatively isolated from fresh PBMCs using the CD4+ T cells negative purification kit according to manufacturer's instructions (Stem Cell Technologies). After isolation, CD4+ T cells were cultured in complete RPMI medium containing 10% fetal bovine serum in the presence of 5 µg/ml PHA (Sigma) and 20 units/ml of recombinant human IL-2 for 24 hrs. at 37° C. under a 5% $CO_2$ atmosphere. After 2 washes, the cells were then maintained for 5-6 days in exponential growth phase on RPMI complete medium containing 20 units/ml human IL-2. After washing and IL-2 starvation for 24 hrs., the above described siRNAs and plasmid DNAs were introduced into cells by electroporation using the LONZA nucleofector 96-well shuttle system for human T cells and program E0-115. Cells were evaluated 24 hrs after transfection.

Example 2

Human LAT is Ubiquitylated at Amino Acid 52

Figures 2A, 2B:
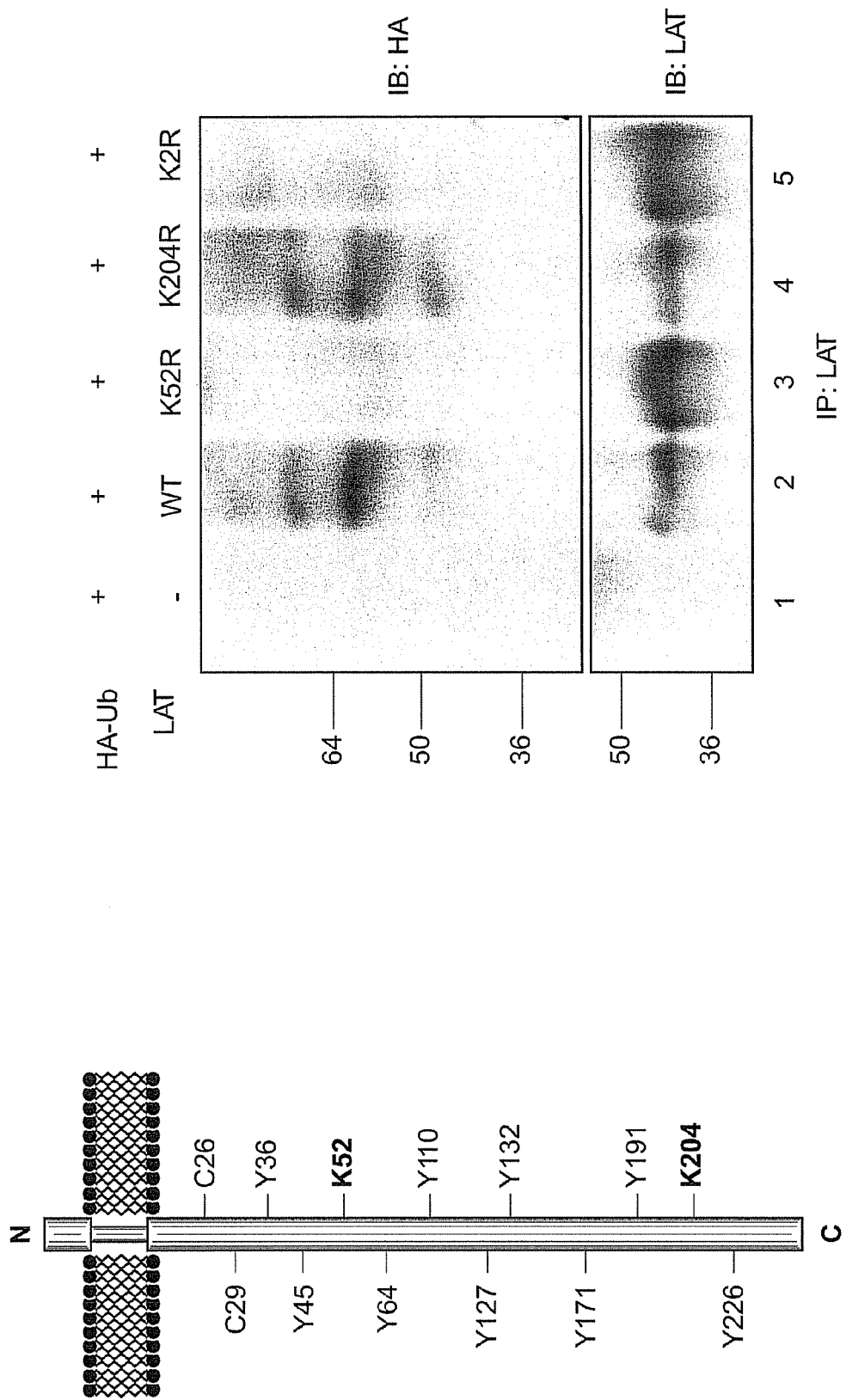
FIG. 2: (A) Schematic of human LAT protein. (B) Western blot of immunoprecipitates from cells transfected with expression vectors encoding an HA-tagged ubiquitin and a wild-type or mutated version of LAT as indicated.

LAT contains a small extracellular domain, a single transmembrane spanning region and a long intracellular region with no apparent intrinsic enzyme activity or commonly described protein-protein interaction domains (FIG. 2A). The intracellular domain of LAT contains nine tyrosines of which five are phosphorylated (Y127, Y132, Y171, Y191, Y226) (Zhu, Jansen, Zhang J I 2003, Paz 2001), and two membrane proximal cysteine residues (C26 and C29) that are subject to posttranslational palmitoylation (Zhang 1998). LAT amino acid sequence also reveals two lysines (K52 and K204 in human LAT) that might serve as potential sites for ubiquitylation. Both LAT lysines were mutated either individually or in combination, and the potential ubiquitylation of these LAT proteins was evaluated. COS-7 cells were transfected with HA-tagged ubiquitin and wild-type (WT) LAT or LAT mutated on lysines, followed by immunoprecipitation of LAT and anti-HA western blotting. Consistent with previously published studies that presented evidence for LAT ubiquitylation (Brignatz 2005, Balagopalan 2007), immunoprecipitation of LAT resulted in the co-precipitation of ubiquitylated bands (FIG. 2B). Strikingly, while the LAT K204R mutant displayed ubiquitylation levels similar to wild-type LAT (FIG. 2B, compare lanes 2 and 4), the LAT K52R mutant immunoprecipitates showed greatly decreased anti-HA reactivity (FIG. 2B, lane 3). Not surprisingly, the LAT 2KR mutant in which both LAT K52 and K204 are mutated also showed decreased ubiquitylation. The decreased HA reactivity is not due to a decrease in levels of expression since the LAT K52R and LAT 2KR mutants were consistently expressed at levels equal to or higher than the wild-type and K204R constructs (FIG. 2B, lower panel). These data indicate that LAT is predominantly ubiquitylated on K52. For the remainder of the experiments in this study we used the LAT 2KR mutant in which both lysines 52 and 204 were mutated.

Example 3

Ubiquitin-Defective LAT is Internalized at Rates Comparable to Wild-Type LAT

To evaluate whether LAT ubiquitylation is required for LAT internalization, we assessed dynamics of wild-type and 2KR LAT. To this end, we tagged wild-type and 2KR LAT with a YFP tag at the carboxy terminus. Jurkat E6.1 cell lines were transfected with either wild-type LAT-YFP or 2KR LAT-YFP and trafficking of the fluorescent LAT constructs was evaluated. Both wild-type and 2KR LAT-YFP were recruited rapidly to signaling clusters in Jurkat E6.1 cells. High-speed microscopic analysis of activated cells in real time revealed that both wild-type LAT-YFP and 2KR LAT-YFP clusters dissipated soon after cluster formation in Jurkat E6.1 cells (FIG. 3). Similar dynamics of LAT-YFP clusters were observed in Jukat JCam2.5 cells that lack endogenous LAT. These data indicate that under conditions of severely reduced ubiquitylation, LAT internalization proceeds at regular rates, suggesting that ubiquitylation of LAT is not required for LAT internalization. Alternatively, the residual ubiquitylation of the 2KR LAT mutant in the absence of major ubiquitylation sites may be sufficient for LAT internalization. We have previously demonstrated that c-Cb1 activity is required for movement of LAT clusters (Balagopalan et al., 2007).

To examine the effect of c-Cb1 expression on 2KR LAT dynamics in living cells, we transfected Jurkat E6.1 cells expressing wild-type or 2KR LAT-YFP, with 70Z/3 Cb1-CFP, an oncogenic, dominant negative version of c-Cb1 with a 17 amino acid internal deletion into the RING finger domain that abrogates ubiquitin ligase activity (Andoniou, C. E., et al, 2000. *Mol. Cell. Biol.* 20:851-867). As shown in FIG. 3, in cells expressing 70Z/3 Cb1-CFP, both wild-type and 2KR LAT clusters persisted for extended periods of time. Thus movement of ubiquitin-defective LAT is regulated by c-Cb1 activity. Taken together, these results suggest that 70Z/3 Cb1 causes persistence of LAT complexes due to defective ubiquitylation of proteins beside LAT. These proteins could potentially be other signaling molecules in the LAT-nucleated signaling complex. Alternatively, endocytic adapter proteins may be the targets of ubiquitylation.

Example 4

Figure 4A:
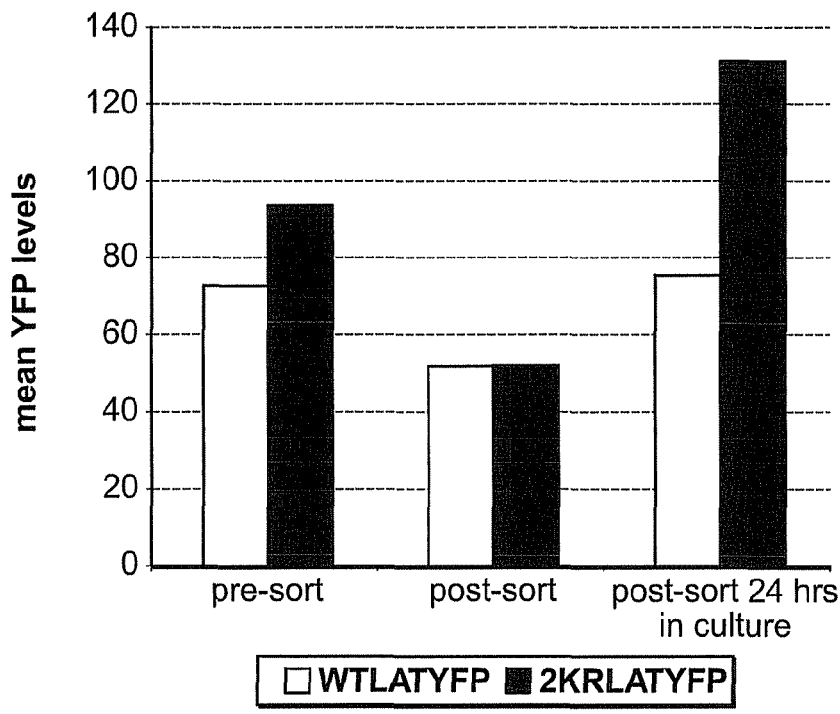
FIG. 4: (A) Mean YFP levels of cells expressing wild-type LAT-YFP or 2KR LAT-YFP 24 hours after transfection pre-sort, post-sort and post-sort 24 hrs in culture (B) Quantitative, real-time PCR results of endogenous LAT, transfected LAT and beta-actin.
Figure 4B:
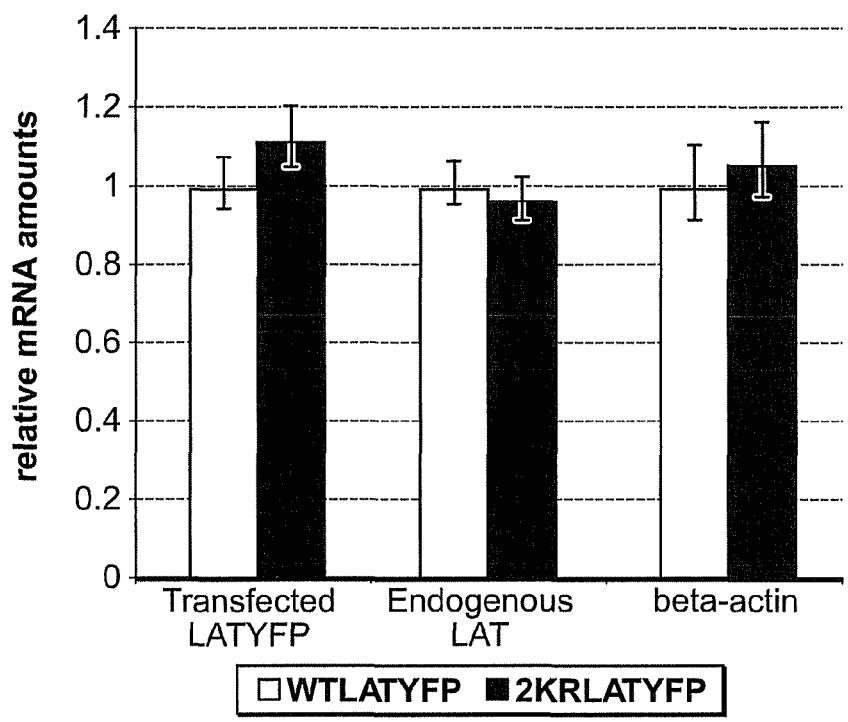

2KR LAT Levels are Higher than Wild-Type LAT Levels in Transiently Transfected Cells Initially, ubiquitylation was described as the process that labels proteins for degradation (Hershko and Ciechanover, 1998). To test whether LAT was regulated in a similar manner, equal amounts wild-type and 2KR LAT-YFP DNA were transiently transfected into E6.1 Jurkat T cells and YFP levels monitored by flow cytometry. 24 hours after transfection, levels of 2KR LAT-YFP were significantly higher than wild-type LAT-YFP. To control for differences in transfection efficiency, cells expressing similar levels of YFP-tagged proteins were sorted. Flow analysis on cells cultured for 24 hours post-sorting revealed that mean 2KR LAT-YFP levels were increased to nearly two-fold higher than wild-type LAT-YFP (FIG. 4A). Higher intracellular protein levels of LAT containing the lysine mutations could reflect increased transcription of the 2KR LAT-YFP construct or increased stability of 2KR LAT-YFP protein. To test the first possibility, relative transcript abundance was evaluated by quantitative RT-PCR. cDNA was prepared from E6.1 cells transiently transfected with wild-type LAT-YFP or 2KR LAT-YFP. Real-time quantitative PCR was performed on both samples for chimeric LAT-YFP and endogenous LAT transcript expression. Transcript levels of the β-actin gene were used as a reference. In these samples, the relative quantification of the wild-type versus the chimeric 2KR LAT-YFP transcripts revealed no significant differences (FIG. 4B). The lack of correlation between transcript and protein levels is suggested to be the consequence of the involvement of post-transcriptional regulations such as protein degradation.

Example 5

Mutation of LAT Lysines Delays LAT Degradation

Figure 5C:
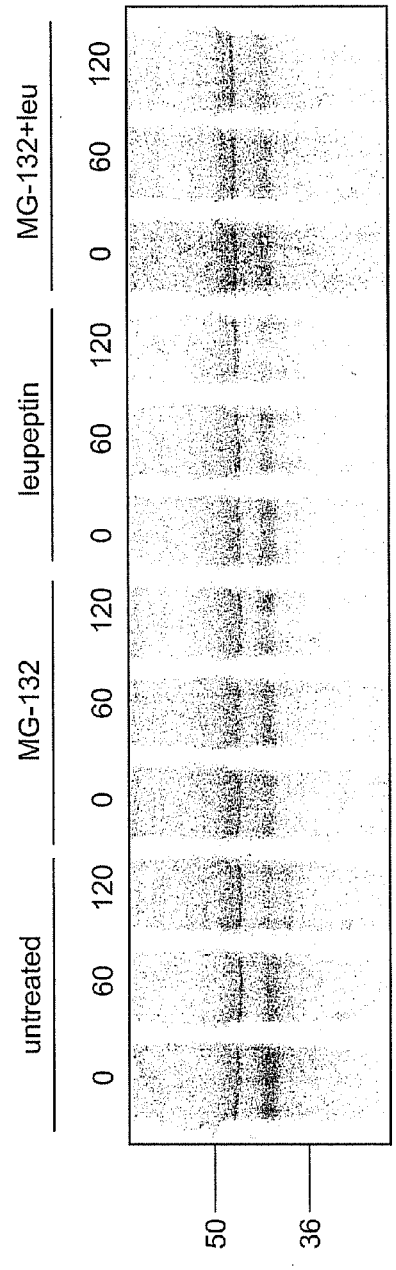
Figure 5B:
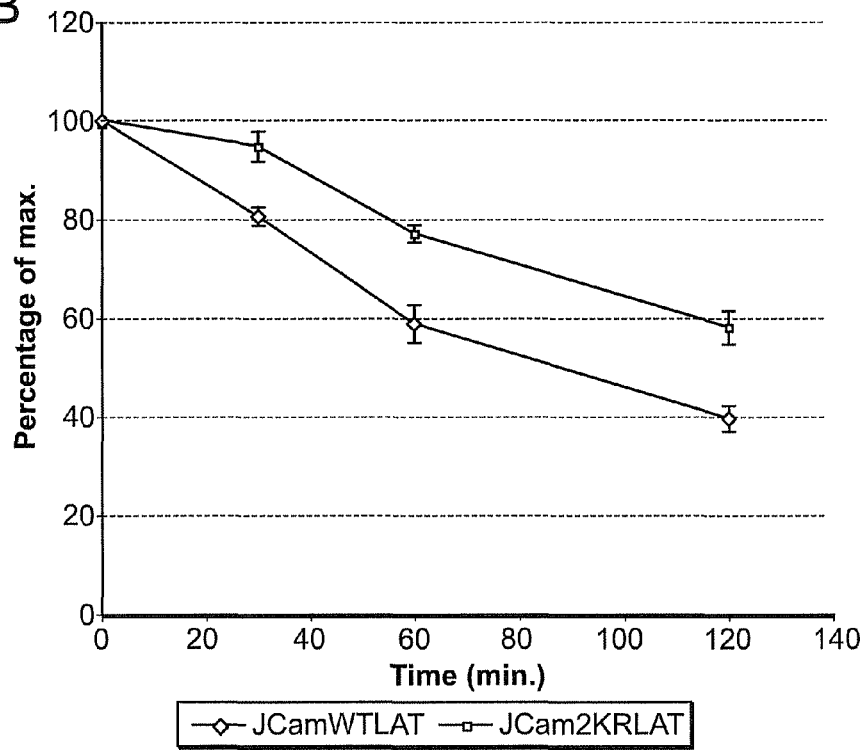
Figure 5D:
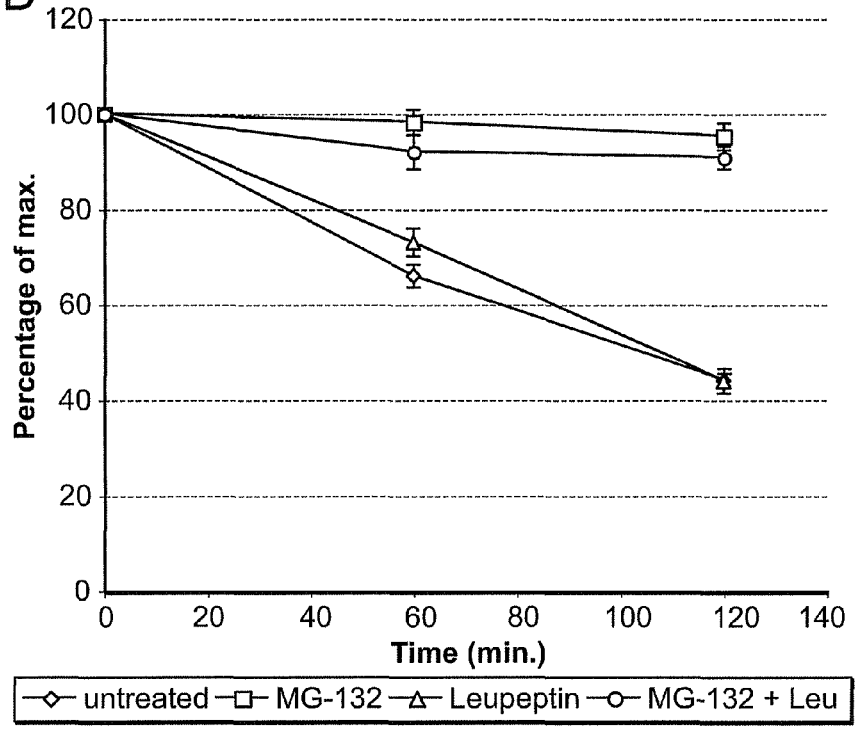

The data in FIG. 4 indicate that 2KR LAT is more stable and resistant to degradation than wild-type LAT. To test this hypothesis directly, pulse-chase analysis was performed on Jurkat JCam2.5 cells that lack endogenous LAT, but stably express either wild-type or 2KR LAT. Briefly, cells were incubated in medium that contained $^{35}$S-labeled methionine and cysteine. Whole cell lysates were prepared at various time-points after the initial pulse and LAT immunoprecipitations were performed. Immunoadsorbed proteins were subjected to SDS-PAGE and analyzed by autoradiography (FIG. 5A). The band above the 36 kDa standard is LAT. The band is absent in LAT-deficient JCam2.5 cells. To quantitate the amount of labeled LAT recovered at each time-point in the chase, the density of the LAT band on autoradiographs was measured by scanning densitometry. The density of the LAT band decreased with time, indicating that the amount of LAT recovered from the lysates decreased during the chase, and likely represents intracellular LAT degradation. Recovery of labeled LAT at 30 minutes, 1 hour and 2 hours was quantified in 4 separate experiments. Based on these data the intracellular half-life of LAT appears to be 70 minutes. In contrast, even at the 120-minute time-point, more than half of 2KR LAT persisted, demonstrating a delay in the degradation of the mutant protein (FIG. 5B). Of note, the lysine mutations did not completely block steady state degradation indicating that other mechanisms of protein degradation may exist for LAT or alternatively, residual ubiquitylation of the lysine mutant drives degradation. Nonetheless, the 2KR mutation afforded LAT significant protection from degradation.

Protein degradation occurs through two main cellular routes: the ubiquitin-proteasome and the autophagy-lysosome pathways (Knecht, Aguado, Saez Cell. Mol Life Sci 2009). As an initial approach to determine which pathway mediates steady state degradation of LAT, cells were preincubated with proteasome (MG-132) or lysosome (leupeptin) inhibitors and subsequently followed by pulse-chase. While degradation of LAT was observed without proteasome inhibitors, its turnover was significantly halted in their presence, revealing that LAT steady state degradation is regulated by the proteasome. In contrast lysosomal inhibition did not have an effect on LAT degradation kinetics (FIGS. 5C and D).

Figure 5E:
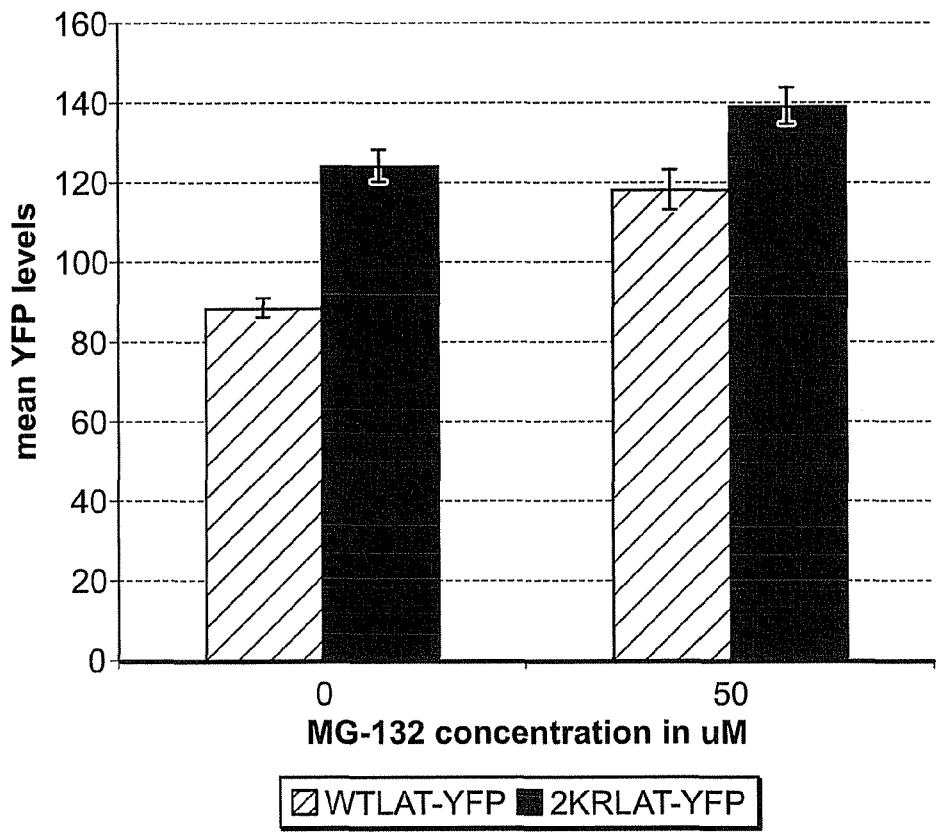

Given these results, we reasoned that proteasomal degradation of wild-type LAT in unstimulated cells could explain the differences in expression levels seen between wild-type and 2KR LAT in FIG. 4. To test this hypothesis, wild-type and 2KR LAT-YFP expressing cells were treated with the proteasomal inhibitor MG-132. Indeed, MG-132 treatment shifted wild-type LAT-YFP expression to levels closer to that of 2KR LAT-YFP expression (FIG. 5E). However, the presence of the proteasome inhibitor also increased the amount of the 2KR mutant observed, consistent with the observation that the lysine mutations do not completely block steady state LAT degradation.

Example 6

Figure 6A:
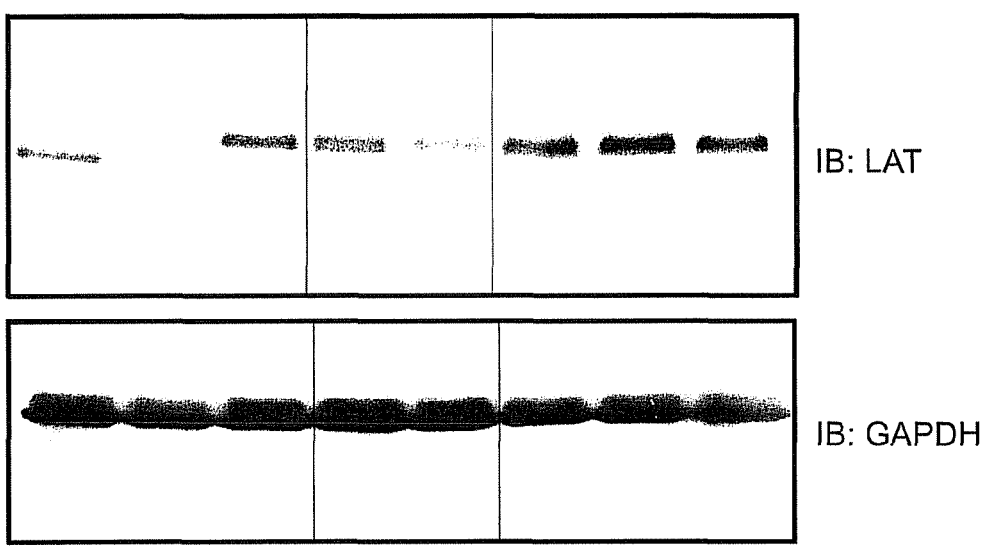
FIG. 6: (A) Western blot analysis of whole cell lysates of LAT-deficient Jurkat JCam2.5 cells stably expressing wild-type or 2KR LAT. (B) Cells were stimulated with CD3 antibody and calcium influx was monitored using a fluorescent dye INDO-1. (C) Cells were stimulated with 10 μg/ml CD3 and CD69 levels were evaluated 16 hours post-stimulation.
Figure 6B:
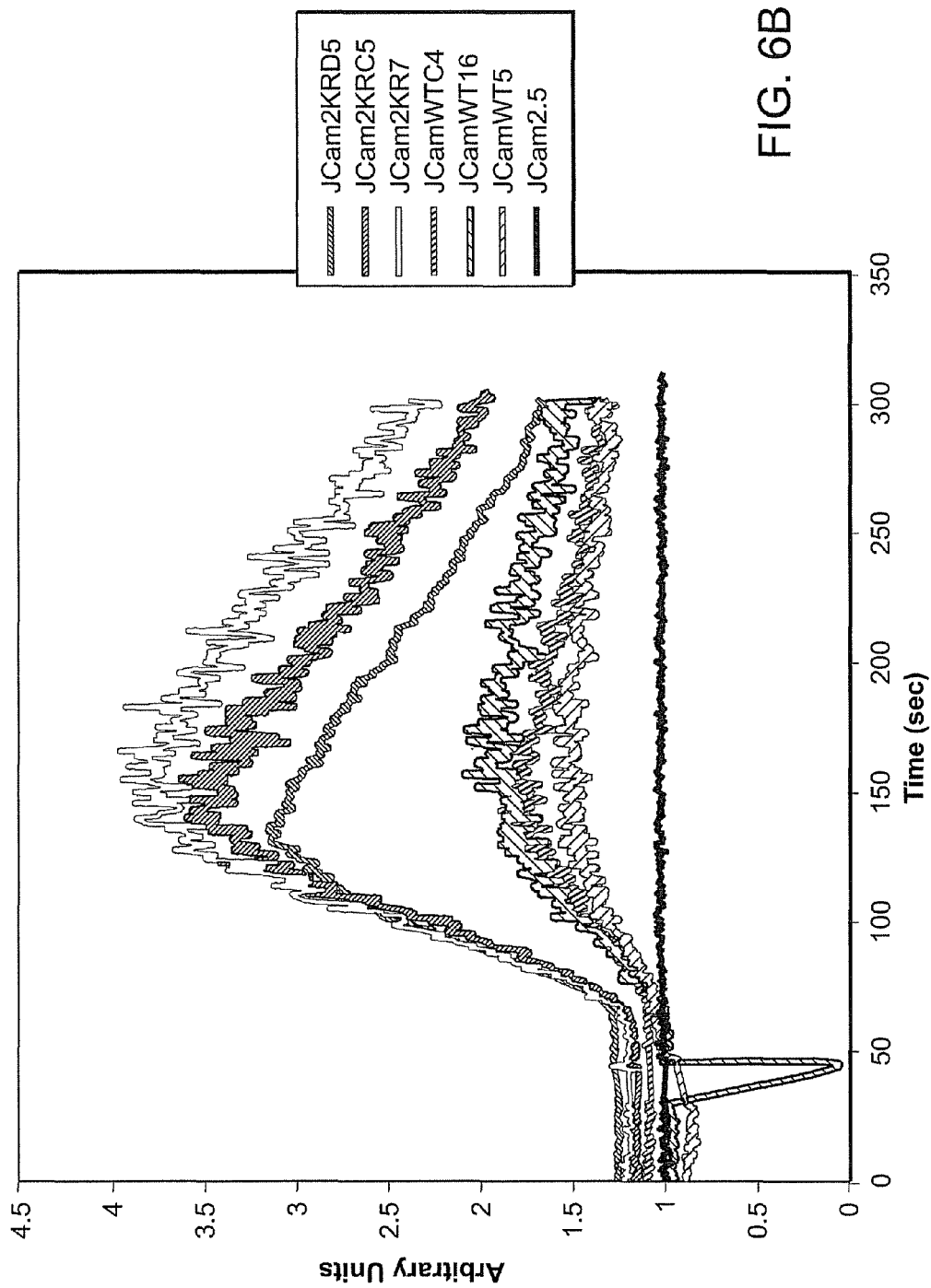

Ubiquitylation Defective LAT Mutant Exhibits Enhanced Signaling Downstream of the TCR Addition of ubiquitin moieties on signaling proteins may serve as a means to regulate the degree and duration of cell activation (Haglund, K. & Dikic, I. *EMBO J.* 24, 2005). To investigate whether increased stability of the LAT 2KR mutant in cells correlates with increased or prolonged signaling by this mutant, signaling assays were performed in cells expressing wild-type or 2KR LAT. JCam2.5 cells lacking endogenous LAT were reconstituted with wild-type or 2KR LAT expressed at various levels (FIG. 6A). First, CD3-dependent cytosolic $Ca^{++}$ flux was evaluated. As reported previously, Jurkat JCam2.5 cells do not display an increase in cytosolic $Ca^{++}$ levels upon CD3 stimulation (Finco 1998, FIG. 6B). Reconstitution of these cells with wild-type LAT led to measurable $Ca^{++}$ flux in all cell lines tested. In comparison, all JCam2.5 cell lines reconstituted with 2KR LAT displayed considerably higher levels of cytosolic $Ca^{++}$ levels in response to stimulation with anti-CD3ε antibodies.

To identify other indicators of TCR signaling in these cells, CD69 levels were measured. CD69 is the one of the first glycoproteins upregulated on the surface of T cells upon TCR stimulation and is known to be dependent on Ras activation. JCam2.5 cells stably transfected with wild-type or 2KR LAT were stimulated with anti-CD3ε antibodies. Sixteen hours post-stimulation, surface CD69 levels were measured by flow cytometry. Prior to stimulation, CD69 levels appeared to be marginally higher in cells containing 2KR LAT. However, upon CD3 stimulation, more profound differences in CD69 expression were observed. Cells expressing 2KR LAT had significantly higher levels of CD69 as compared with cells expressing wild-type LAT (FIG. 6C). Together, these data demonstrate that signaling pathways downstream of the TCR are enhanced in cells that express ubiquitin-defective 2KR LAT.

An observation apparent from the data in FIG. 6A is that in JCam2.5 cell lines stably expressing wild-type or mutant LAT, 2KR levels were higher in all cell lines examined. This is probably due to enhanced stability of the lysine mutant protein as demonstrated in FIG. 4. Therefore it was not possible to determine whether the increased biologic signaling by LAT mutated on lysines was due to higher protein levels in the 2KR reconstituted JCam2.5 cells or due to increased signaling properties of the 2KR LAT mutant per se. To address this issue, JCam2.5 cells were transfected with expression constructs for the expression of YFP-tagged wild-type or 2KR LAT. We reasoned that gating on equivalent levels of expression of YFP tagged proteins would enable us to evaluate signaling in cells expressing equal levels of wild-type or mutant LAT. However, transient expression of YFP-tagged proteins in JCam2.5 cells, at levels no more than two-fold higher than endogenous LAT expression in E6.1 cells, did not reconstitute CD3-stimulated signaling. To circumvent these issues, a knock-down re-expression system was employed in Jurkat E6.1 cells as described below.

Example 7

Figure 7B:
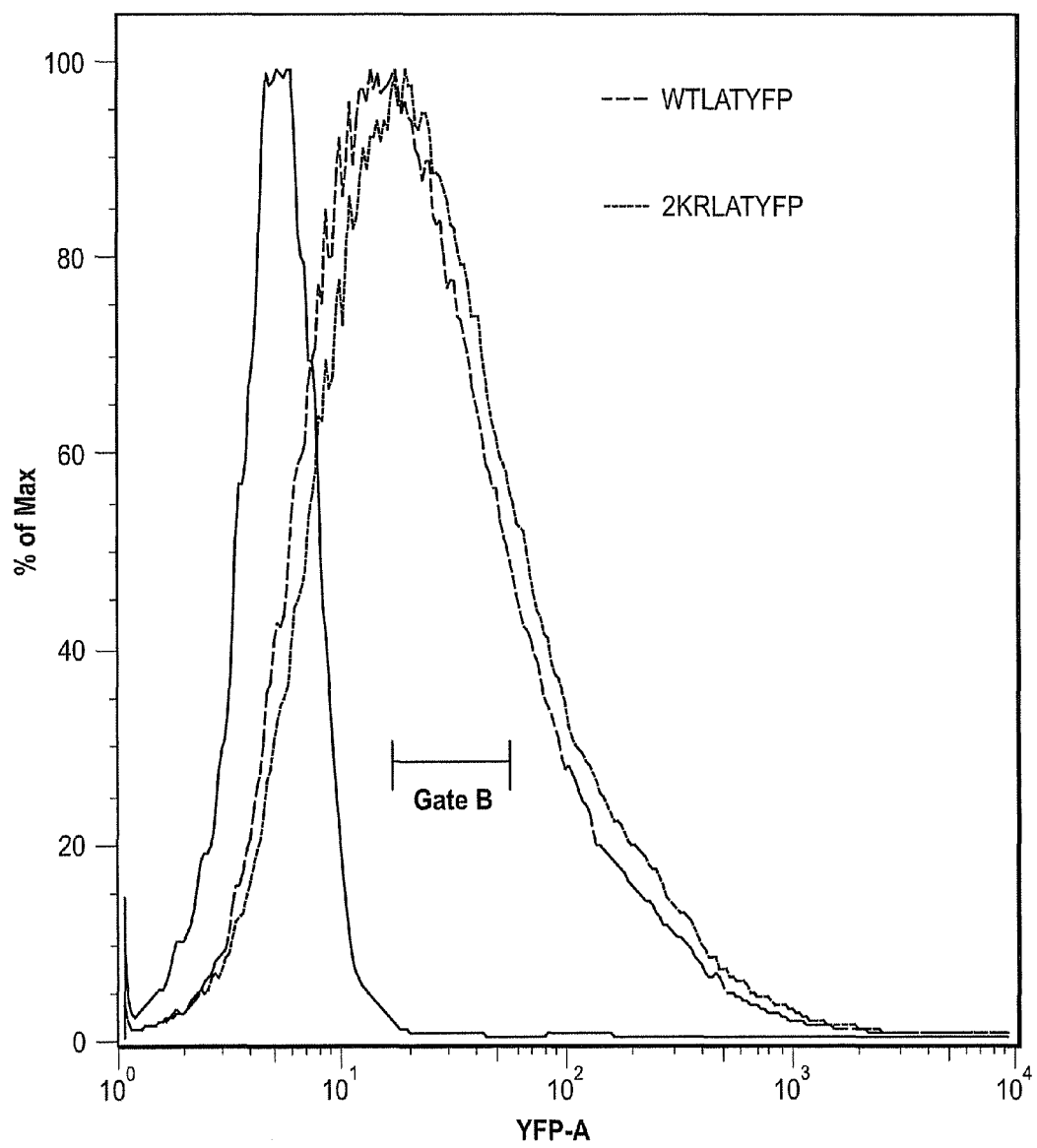
FIG. 7: Jurkat E6.1 cells were transiently transfected with LAT targeting siRNA or control siRNA and control YFP plasmid, wild-type LAT-YFP or 2KR LAT-YFP plasmids as indicated. (A) Whole cell lysates were prepared from the above-described transfected cells 48 hours after transfection. The levels of endogenous LAT, transfected LAT-YFP (upper panel) and β-actin (lower panel) were assessed by immunoblotting (B) Histogram showing wild-type LAT-YFP and 2KR LAT-YFP expression. For functional assays described in C and D, cells falling within Gate B expressing equivalent levels of LAT-YFP protein were analyzed. (C) Transfected cells were stimulated with CD3 and cytosolic $Ca^{++}$ influx was measured. (D) CD69 upregulation was measured in transfected cells 18 hrs after CD3 activation. (E) NFAT luciferase activity was measured in cells stimulated with various doses of CD3.
Figure 7C:
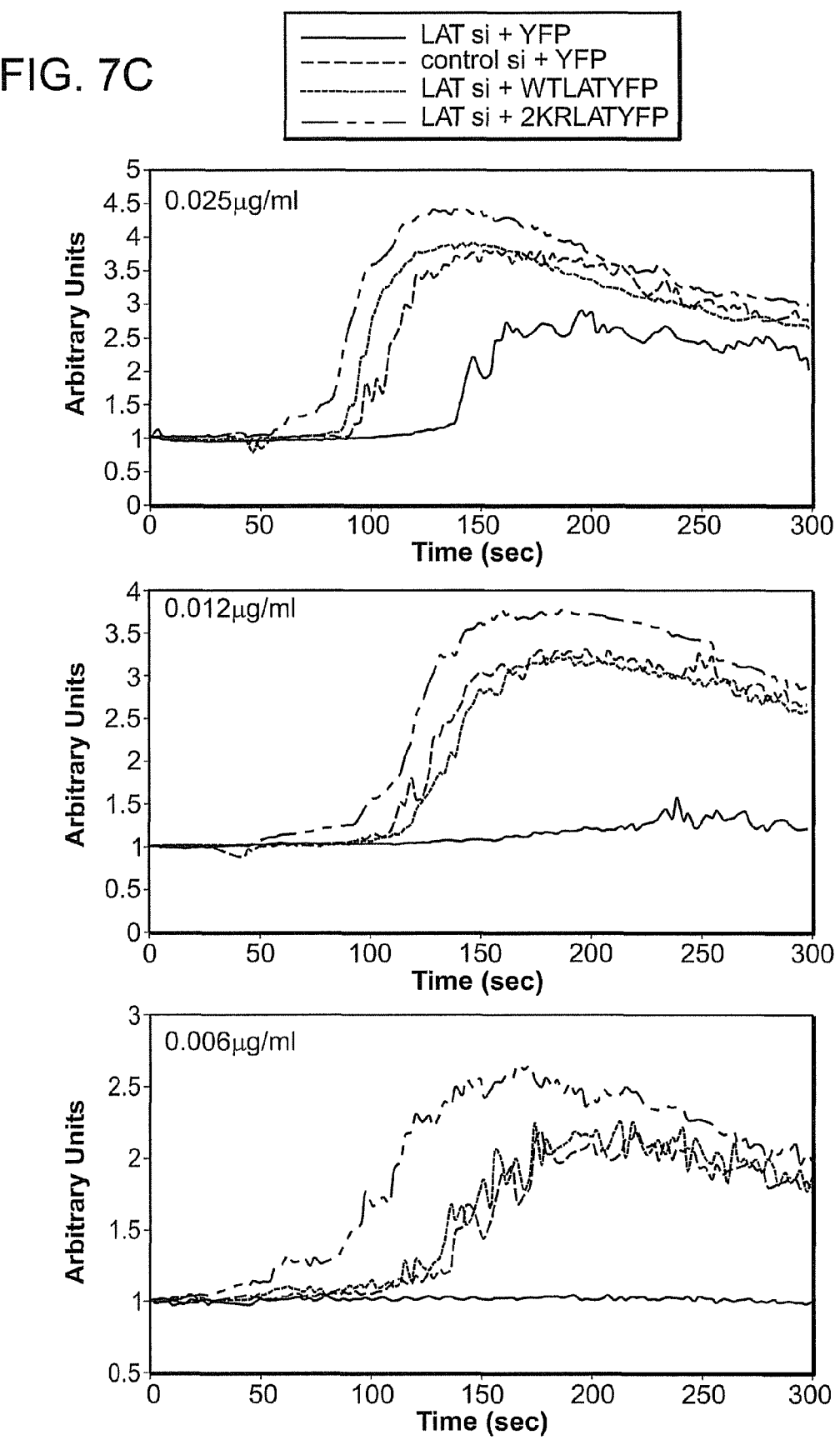

CD69 Level Upregulation Mediated by TCR Activation is Higher in Cells Expressing Ubiquitin-Defective LAT RNA-mediated interference was employed to genetically silence endogenous LAT expression in Jurkat E6.1 cells. Simultaneously, either YFP, wild-type or 2KR LAT-YFP was re-expressed in these cells. 48 hours after transfection, whole cell lysates were prepared and subject to electropheresis and immunoblotting for LAT. As shown in FIG. 7A, expression of siRNA targeting LAT dramatically reduced endogenous LAT expression, in comparison to LAT expression in Jurkat E6.1 cells or control siRNA transfected cells. Fluorescence activated cell sorting (FACS) analysis of the YFP-tagged proteins at 48 hours showed higher levels of 2KR LAT-YFP expression as expected (FIG. 7B). However, the YFP tag enabled us to gate on cells expressing equal amounts of the YFP tag (Gate B), corresponding to equivalent levels of LAT. To test the consequence of disruption of LAT ubiquitylation for signaling events, TCR-induced $Ca^{++}$ influx was examined at three different concentrations of CD3 stimulation (FIG. 7C). Transfection of LAT targeting siRNA showed reduced $Ca^{++}$ flux as compared with control siRNA at all three concentrations. At 0.025 ug/ml and 0.012 ug/ml anti-CD3 a slight $Ca^{++}$ flux remained, but no detectable $Ca^{++}$ flux occurred at 0.006 ug/ml, indicating that endogenous LAT no longer contributed to cytosolic $Ca^{++}$ flux at this stimulation dose. In comparison, expression of wild-type LAT-YFP showed similar levels of $Ca^{++}$ flux as control siRNA transfected cells at all concentrations tested. Strikingly, LAT depleted cells reconstituted with 2KR LAT-YFP showed increased cytosolic flux at all CD3 doses. Notably, the effect of mutations of LAT lysines was greater at the lower abundance of soluble anti-CD3 than at the higher concentrations. This suggests that LAT ubiquitylation has a more prominent role in regulation of TCR-mediated signaling under limiting stimulatory conditions.

Figure 7D:
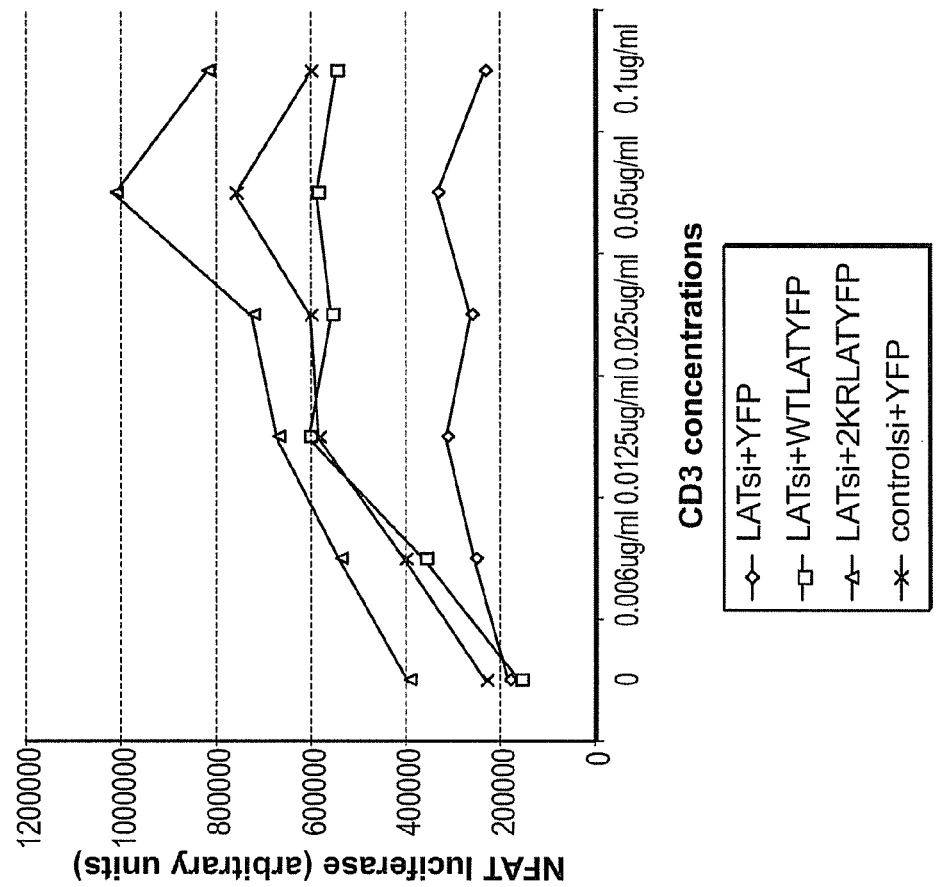
Figure 7E:
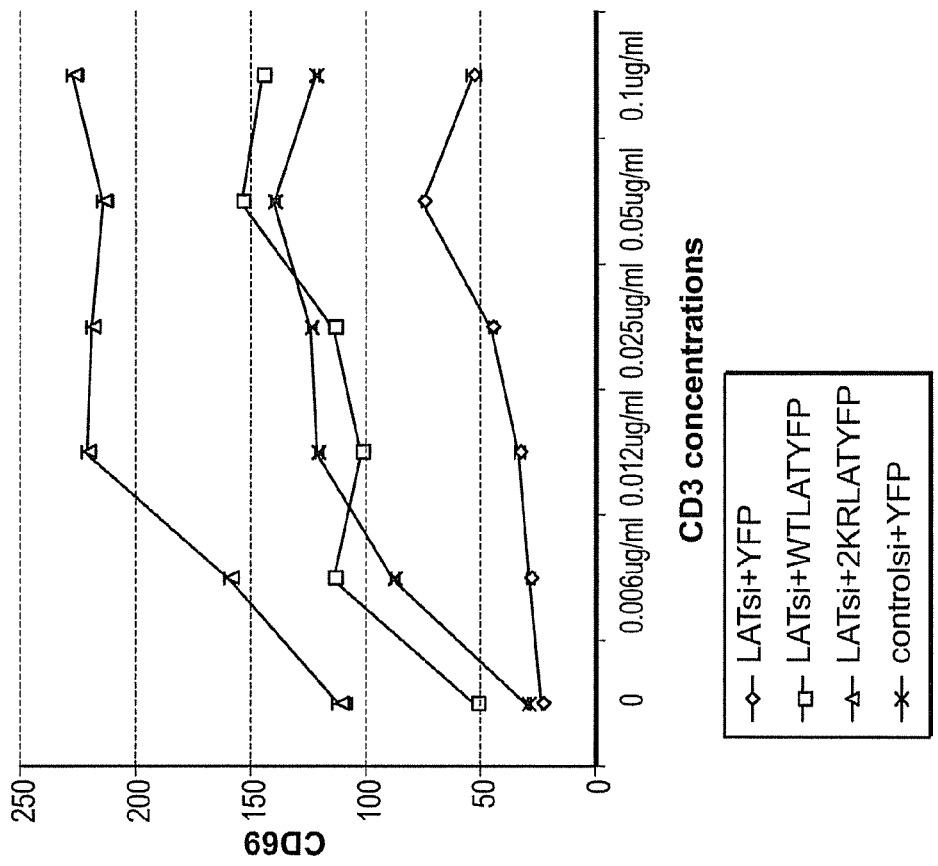

Increases in intracellular $Ca^{++}$ concentrations upon TCR engagement controls various signaling pathways, importantly including activation of the transcription factor NFAT. Therefore the LAT expressing cells were subjected to NFAT luciferase assays. Under all stimulation conditions tested, LAT-depleted cells reconstituted with 2KR LAT showed elevated signaling compared with cells reconstituted with its wild-type counterpart (FIG. 7D). We also checked for other indicators of TCR signaling such as CD69 upregulation. Anti-CD3 induced CD69 upregulation was also enhanced at all doses of anti-CD3ε antibody in cells reconstituted with 2KR LAT (FIG. 7E). Importantly, we evaluated signaling output on cells expressing equivalent levels of wild-type and 2KR LAT-YFP in the above-described functional assays evaluating $Ca^{++}$ influx and CD69 upregulation. These data allow us to conclude that 2KR LAT possesses more potent signaling properties and can cause T cell activation more effectively on a per molecule basis as compared with wild-type LAT.

Example 8

Figure 8B:
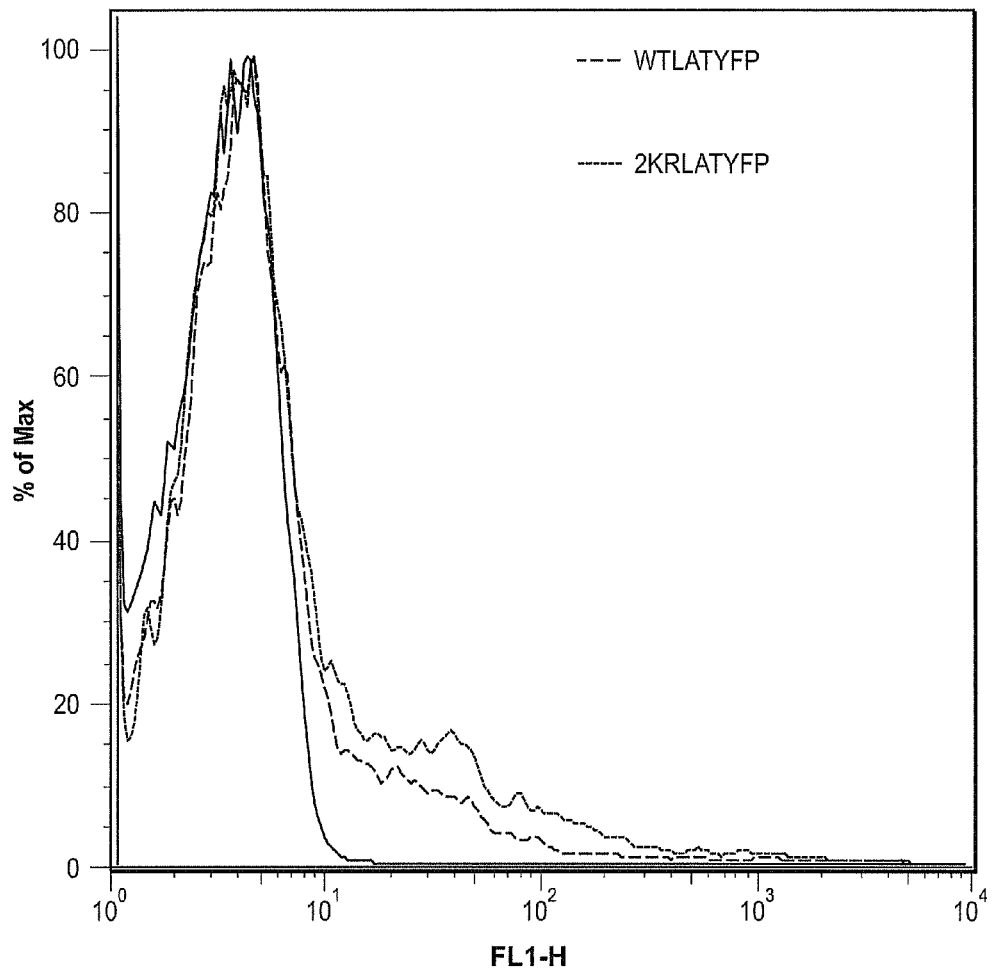
FIG. 8: Primary human CD4+ cells were transiently transfected with LAT targeting siRNA or control siRNA and control YFP plasmid, wild-type LAT-YFP or 2KR LAT-YFP plasmids as indicated. (A) Whole cell lysates were prepared from the above-described transfected cells 48 hours after transfection. The levels of endogenous LAT, transfected LAT-YFP (upper panel) and β-actin (lower panel) were assessed by immunoblotting (B) Histogram showing wild-type LAT-YFP and 2KR LAT-YFP expression. (C) CD69 upregulation was measured in transfected cells 18 hrs after CD3 activation.

Evaluation of TCR Signaling in LAT Knockdown Cells Reconstituted with Wild-Type or 2KR Mutant LAT To confirm that the effects of 2KR expression occurred in non-transformed cells, we performed experiments in primary human T cells. CD4+ T cells were isolated from freshly isolated PBMCs of healthy donors. CD4+ cells were transfected with control siRNA or LAT targeting siRNA and simultaneously with plasmids expressing YFP, wild-type LAT-YFP or 2KR LAT-YFP as indicated. Similar to the experiments performed in Jurkat cells, 2KR LAT expression levels were consistently higher than wild-type LAT (FIG. 8B). Western blot analysis of lysates from sorted YFP-positive cells was performed to assess both the efficiency of the siRNA knockdown and levels of re-expressed wild-type and 2KR LAT-YFP. As shown in FIG. 8A, a knockdown of 35% of endogenous LAT was achieved in these cells.

Although not as efficient as LAT knockdown in Jurkat E6.1 cells, the functional effects of 2KR LAT expression were tested by gating on YFP expressing cells. Transfected cells were incubated with various concentrations of anti-CD3 and anti-CD28 antibodies and evaluated for CD69 upregulation at 16 hours post-stimulation. Of note, the doses of CD3 had to be increased to see robust CD69 upregulation in primary cells, as compared with the doses used in Jurkat cells. Nevertheless, consistent with observations made in Jurkat cells, we saw enhanced CD69 upregulation in cells expressing 2KR LAT at all concentrations tested (FIG. 8C). Interestingly, the differences between 2KR LAT, wild-type LAT and cells in which LAT was depleted was most apparent at lower doses of stimulation, in agreement with our conclusion that LAT ubiquitylation plays a more significant role in TCR activation under limiting stimulatory conditions. Taken together, these data support the conclusion that LAT is targeted by ubiquitylation within lysines and that these events coordinately downregulate LAT-dependent TCR signaling events.

Example 9

Knockdown of LAT Levels Using shRNAs

To further analyze the role of LAT levels in signaling downstream of the TCR, siRNAs and shRNAs targeted to LAT were designed and transfected in Jurkat E6.1 cells. As shown in FIG. 9A, cells transfected with a non-targeting siRNA showed a robust influx of cytosolic $Ca^{++}$ upon CD3 stimulation. In contrast, transfection with either a pool of 4 siRNAs targeting LAT (siPool) or a single LAT targeting siRNA (si2 and si4) effectively abrogated cytosolic $Ca^{++}$ flux. Of note, siRNA targeting of LAT caused a 80-90% decrease in LAT levels as evaluated by western blot.

To enable us to evaluate the effect of decreasing LAT levels in a controlled manner, we generated plasmids in which shRNA to LAT and GFP were expressed simultaneously. This expression system allowed for cell sorting with gating based on GFP expression in the cell. Higher GFP levels correlates with higher shRNA expression and thus, inversely correlates with LAT protein levels. Of note, LAT protein level in cells included in gate C (GC) in FIGS. 9B and C corresponds to background levels of LAT expression in LAT deficient Jurkat JCam2.5 cells. Jurkat E6.1 cells were transfected with shRNA GFP plasmids and cytosolic $Ca^{++}$ influx was measured in cells gated into three groups based on increasing GFP expression: gate A (GA), gate B (GB) and gate C (GC). Of interest, higher levels of GFP in the cell corresponded with decreased Ca$^{++}$ influx in response to CD3 stimulation (FIGS. 8B and C). These data demonstrate that LAT expression has a dose-dependent effect on proximal signaling downstream of the TCR. This result is consistent with increased signaling observed in cells expressing LAT 2KR mutant that has a degradation defect and accumulates to higher levels in cells.

Jurkat E6.1 cells in which LAT has been knocked down by the shRNA GFP expression system described are reconstituted with wild-type or 2KR LAT tagged with a fluorescent protein. This knockdown re-expression system enables us to evaluate the effects of increasing levels of LAT knockdown by gating on GFP levels and at the same time evaluate the effect of reconstitution of different levels of wild-type and mutant LAT in the knockdown cells. This experiment gives us an entire matrix of information from which we can evaluate the effects of reconstitution of particular doses of wild-type and 2KR LAT at a given dose of LAT knockdown. Thus, by gating on equal levels of reconstituted wild-type or mutant protein at a given level of knockdown, we are able to investigate whether the 2KR LAT is a more potent signaling molecule, or whether the increased signaling in the 2KR cells is due to increased levels of LAT expression, or a combination of the two. Various readouts are used for evaluating TCR signaling such as cytosolic Ca$^{++}$ influx, CD69 levels, CD25 levels, NFAT and NF-KB luciferase assays, intracellular IL-2 levels and levels of phosphorylated signaling proteins.

Example 10

Evaluation of TCR Signaling in Primary Human T Cells with LAT Knocked Down and Reconstituted with Wild-Type or 2KR Mutant LAT Primary human PBLs are transfected with LAT knockdown constructs and wild-type or 2KR LAT as described above for expression in Jurkat cells. Results from Jurkat E6.1 cells are confirmed in primary T cells. It is expected that the expression of wild-type or ubiquitin defective LAT, or inhibition of expression of LAT, has the same effect on T-cell signaling in primary cells as in Jurkat cells.

Example 11

Evaluation of TCR Signaling in Peripheral T Cells in 2KR LAT Transgenic Mice

To investigate the role of LAT ubiquitylation in vivo, we have generated transgenic mice expressing wild-type and ubiquitin-defective LAT. Methods to generate transgenic mice are well known in the art, see, e.g., *Manipulating the Mouse Embryo: A Laboratory Manual* (Andras Nagy et al., Cold Spring Harbor Laboratory Press; 3 edition, 2002). The transgenic mice and cells from the transgenic mice are used to investigate signaling in various T cell populations and compared to mice expressing wild-type LAT. Wild-type and ubiquitin defective LAT was expressed at various levels under the control of the distal Lck promoter, which is expressed late in thymic development, to get expression in mature T cells, thus enabling us to avoid thymic selection which might eliminate more potent T cells. Expression in mature T cells bypasses this developmental process.

Analysis of 2KR LAT transgenic mice demonstrate that mature 2KR LAT containing T cells have enhanced TCR-dependent signaling compared with their wild-type counterparts.

Example 12

Evaluation of T Cell Development in 2KR LAT Transgenic Mice

Transgenic mice expressing a ubiquitin-defective LAT protein, e.g., 2KR LAT are generated using routine methods. To investigate the role of LAT ubiquitylation in T cell development, wild-type and 2KR LAT are expressed under the control of the human CD2 promoter that expresses early in development. T cell development is evaluated by assessment of various cell surface markers such as CD4 and CD8. If the numbers as assessed by these markers are different from those seen in wild type mice at various stages of development, we conclude that T cell development is affected by the LAT 2KR mutation. However, if the numbers of cells at various stages of development are the same, it is still possible that development is affected, but the effects on positive and negative selection cancel each other out. Therefore, positive and negative selection is also evaluated by crossing wild-type and 2KR transgenic mice onto the histocompatibility Y antigen (HY)-TCR transgenic background in which the female mice exhibit positive selection of T cells bearing the Tg TCR, while the male mice show negative selection of such T cells.

Example 13

Evaluation of Anti-Viral and Anti-Tumor Function of 2KR LAT T Cells in Mouse Models Wild-type and 2KR LAT transgenic mice are exposed to viral challenge, carcinogenic insult, and/or implanted with a xenograft tumor. The ability of T cells in these mice to effectively respond to these challenges is evaluated. Normal mice are used for controls in these experiments. In addition mice bearing only transgenic T cell receptors are crossed to the LAT transgenic animal and these mice bearing transgenic TCRs as well as wild-type or 2KR LAT are used for both cancer and viral infection models. These transgenic antigen receptors are specific for known cancer or viruses. It is expected that the presence of the 2KR LAT mutation will enhance clearance of tumor and/or viruses and thus results in a superior response both in the setting of the normal immune response in the case of normal animals and the response of specific TCRs in the case of the transgenic mice.

Various mouse models of viral infection are used. For LCMV acute infection experiments, wild-type and 2KR transgenic mice are infected with various doses of virus (2×105 pfu of LCMV Armstrong strain i.p.). Viral titers are determined by standard plaque assay at various times after initial infection. In addition, response to viral infections are measured by evaluating numbers of virus-specific CD8+ T cells in spleen over time, levels of IFN-☐ produced and cytolytic activity of CD8+ T cells.

Various tumor models are used. For lung cancer model, TC1 cells are injected into mice sub-cutaneously. For tumor clearance experiments, tumor diameters are measured 1-4 weeks after implantation, tumor volumes are calculated, and mouse viability is tracked. Numbers of tumor-specific CD8+ cells are measured using specific reagents (tetramers), levels of IFN-☐ produced and cytolytic activity of these T cells are measured. In addition, melanoma, prostate, breast and other tumor models are tested.

It is expected that 2KR transgenic mice will have better viral and tumor clearance than wild-type LAT expressing mice.

In addition, mice bearing only transgenic T cell receptors are crossed to LAT transgenic animals and mice bearing transgenic TCRs as well as wild-type or 2KR LAT are used for both cancer and viral infection models. These transgenic antigen receptors are specific for known cancer or viruses and have been reported to have moderate effects on tumor or viral clearance. It is expected that the presence of the 2KR LAT mutation will enhance clearance of tumor and/or viruses as assessed above. In some cases, RAG KO mice are exposed to viral or tumor challenge. This allows comparison of antitumor or antiviral effects of pure populations of CD4 and CD8 cells against the same tumor antigen in the absence of other T cells. One day after challenge, mice receive cells from freshly isolated spleens or lymph nodes of the TCR transgenic mice specific for the tumor or viral antigen and containing various doses of wild-type or 2KR LAT. Viral and tumor clearance are evaluated as described above.

Example 14

Evaluation of Ability of 2KR LAT to More Effectively Cause Cancer Regression in Subjects with Metastatic Melanoma Highly selected tumor-reactive T cells directed against overexpressed self-derived differentiation antigens are used for adoptive transfer approaches to combat metastatic melanoma are transfected/transduced with 2KR LAT. Transferred cells are monitored in vivo for their ability to proliferate, traffic to tumor sites and display functional activity. Regression rates of the subjects' metastatic melanoma are evaluated.

Example 15

Evaluation of Signaling, Anti-Viral and Anti-Tumor Function of 2KR LAT in Genetically Engineered T Cells Adoptive immunotherapy is a promising approach for the treatment of melanoma and some other cancers. This approach overcomes the difficulties associated with the isolation and expansion of tumor-reactive T cells in cancer patients. Instead, peripheral blood T cells are retargeted to any chosen tumor antigen by the genetic transfer of an antigen-specific receptor. The transduced receptors may be chimeric antigen receptors (CARs), designed to ligate tumor-associated antigens using antibody fragments fused to a component of the TCR complex, or human leukocyte antigen-restricted, heterodimeric T-cell antigen receptor (TCRs).

Wild-type and 2KR constructs have been cloned into RNA transcription and lentiviral expression vectors. Chimeric Antigen Receptor (CAR) expressing T cells are transduced with wild-type or 2KR LAT and various signaling outputs such as CD69 upregulation and IL-2 production are evaluated upon stimulation via CD3 or surrogate antigen. Wild-type and 2KR LAT are also tested in the context of CAR or MHCI restricted TCRs in vivo in mouse tumor models to evaluate anti-tumor efficacy. The presence of the 2KR LAT mutation enhances the clearance of tumors, reducing tumor burden and extending life.

Those skilled in the art will recognize, or be able to ascertain using no more than routine experimentation, many equivalents to the specific embodiments of the invention described herein. Such equivalents are intended to be encompassed by the following claims.

REFERENCES

All references, patents, patent publications, and sequence reference numbers cited herein are incorporated herein by reference.

Aguilar, R. C., and B. Wendland. 2003. Ubiquitin: not just for proteasomes anymore. Curr. Opin. Cell Biol. 15:184-190.

Alarcon, B., and M. Fresno. 1998. Transferrin receptor (CD71), p. 2389-2392. In P. J. Delves and I. M. Roitt (ed.), Encyclopedia of immunology, $2^{nd}$ ed. Academic Press, London, United Kingdom.

Andoniou, C. E., N. L. Lill, C. B. Thien, M. L. Lupher, Jr., S. Ota, D. D. Bowtell, R. M. Scaife, W. Y. Langdon, and H. Band. 2000. The Cbl protooncogene product negatively regulates the Src-family tyrosine kinase Fyn by enhancing its degradation. Mol. Cell. Biol. 20:851-867.

Andoniou, C. E., C. B. Thien, and W. Y. Langdon. 1994. Tumour induction by activated abl involves tyrosine phosphorylation of the product of the cbl oncogene. EMBO J. 13:4515-4523.

Barda-Saad, M., A. Braiman, R. Titerence, S. C. Bunnell, V. A. Barr, and L. E. Samelson. 2005. Dynamic molecular interactions linking the T cell antigen receptor to the actin cytoskeleton. Nat. Immunol. 6:80-89.

Barr, V. A., L. Balagopalan, M. Barda-Saad, R. Polishchuk, H. Boukari, S. C. Bunnell, K. M. Bernot, Y. Toda, R. Nossal, and L. E. Samelson. 2006. T-cell antigen receptor-induced signaling complexes: internalization via a cholesterol-dependent endocytic pathway. Traffic 7:1143-1162.

Bonello, G., N. Blanchard, M. C. Montoya, E. Aguado, C. Langlet, H. T. He, S, Nunez-Cruz, M. Malissen, F. Sanchez-Madrid, D. Olive, C. Hivroz, and Y. Collette. 2004. Dynamic recruitment of the adaptor protein LAT: LAT exists in two distinct intracellular pools and controls its own recruitment. J. Cell Sci. 117:1009-1016.

Braiman, A., M. Barda-Saad, C. L. Sommers, and L. E. Samelson. 2006. Recruitment and activation of PLCγ1 in T cells: a new insight into old domains. EMBO J. 25:774-784.

Brignatz, C., A. Restouin, G. Bonello, D. Olive, and Y. Collette. 2005. Evidences for ubiquitination and intracellular trafficking of LAT, the linker of activated T cells. Biochim. Biophys. Acta 1746:108-115.

Bunnell, S. C., D. I. Hong, J. R. Kardon, T. Yamazaki, C. J. McGlade, V. A. Barr, and L. E. Samelson. 2002. T cell receptor ligation induces the formation of dynamically regulated signaling assemblies. J. Cell Biol. 158:1263-1275.

Campi, G., R. Varma, and M. L. Dustin. 2005. Actin and agonist MHC peptide complex-dependent T cell receptor microclusters as scaffolds for signaling. J. Exp. Med. 202: 1031-1036.

Douglass, A. D., and R. D. Vale. 2005. Single-molecule microscopy reveals plasma membrane microdomains created by protein-protein networks that exclude or trap signaling molecules in T cells. Cell 121:937-950.

Duan, L., A. L. Reddi, A. Ghosh, M. Dimri, and H. Band. 2004. The Cbl family and other ubiquitin ligases: destructive forces in control of antigen receptor signaling. Immunity 21:7-17.

Dunn, R., and L. Hicke. 2001. Multiple roles for Rsp5p-dependent ubiquitination at the internalization step of endocytosis. J. Biol. Chem. 276:25974-25981.

Ehrlich, L. I., P. J. Ebert, M. F. Krummel, A. Weiss, and M. M. Davis. 2002. Dynamics of p56lck translocation to the T cell immunological synapse following agonist and antagonist stimulation. Immunity 17:809-822.

Fang, D., and Y. C. Liu. 2001. Proteolysis-independent regulation of PI3K by Cbl-b-mediated ubiquitination in T cells. Nat. Immunol. 2:870-875.

Geisler, C. 2004. TCR trafficking in resting and stimulated T cells. Crit. Rev. Immunol. 24:67-86.

Govers, R., T. ten Broeke, P. van Kerkhof, A. L. Schwartz, and G. J. Strous. 1999. Identification of a novel ubiquitin conjugation motif, required for ligand-induced internalization of the growth hormone receptor. EMBO J. 18:28-36.

Haglund, K., P. P. Di Fiore, and I. Dikic. 2003. Distinct monoubiquitin signals in receptor endocytosis. Trends Biochem. Sci. 28:598-603.

Hartgroves, L. C., J. Lin, H. Langen, T. Zech, A. Weiss, and T. Harder. 2003. Synergistic assembly of linker for activation of T cells signaling protein complexes in T cell plasma membrane domains. J. Biol. Chem. 278:20389-20394.

Heissmeyer, V., F. Macian, S. H. Im, R. Varma, S. Feske, K. Venuprasad, H. Gu, Y. C. Liu, M. L. Dustin, and A. Rao. 2004. Calcineurin imposes T cell unresponsiveness through targeted proteolysis of signaling proteins. Nat. Immunol. 5:255-265.

Hicke, L., and R. Dunn. 2003. Regulation of membrane protein transport by ubiquitin and ubiquitin-binding proteins. Annu. Rev. Cell Dev. Biol. 19:141-172.

Houtman, J. C., R. A. Houghtling, M. Barda-Saad, Y. Toda, and L. E. Samelson. 2005. Early phosphorylation kinetics of proteins involved in proximal TCR-mediated signaling pathways. J. Immunol. 175:2449-2458.

Houtman, J. C., H. Yamaguchi, M. Barda-Saad, A. Braiman, B. Bowden, E. Appella, P. Schuck, and L. E. Samelson. 2006. Oligomerization of signaling complexes by the multipoint binding of GRB2 to both LAT and SOS1. Nat. Struct. Mol. Biol. 13:798-805.

Jang, I. K., and H. Gu. 2003. Negative regulation of TCR signaling and T-cell activation by selective protein degradation. Curr. Opin. Immunol. 15:315-320.

Jeon, M. S., A. Atfield, K. Venuprasad, C. Krawczyk, R. Sarao, C. Elly, C. Yang, S. Arya, K. Bachmaier, L. Su, D. Bouchard, R. Jones, M. Gronski, P. Ohashi, T. Wada, D. Bloom, C. G. Fathman, Y. C. Liu, and J. M. Penninger. 2004. Essential role of the E3 ubiquitin ligase Cbl-b in T cell anergy induction. Immunity 21:167-177.

Keane, M. M., S. A. Ettenberg, M. M. Nau, P. Banerjee, M. Cuello, J. Penninger, and S. Lipkowitz. 1999. cbl-3: a new mammalian cbl family protein. Oncogene 18:3365-3375.

Lee, K. H., A. R. Dinner, C. Tu, G. Campi, S. Raychaudhuri, R. Varma, T. N. Sims, W. R. Burack, H. Wu, J. Wang, O. Kanagawa, M. Markiewicz, P. M. Allen, M. L. Dustin, A. K. Chakraborty, and A. S. Shaw. 2003. The immunological synapse balances T cell receptor signaling and degradation. Science 302:1218-1222.

Lupher, M. L., Jr., Z. Songyang, S. E. Shoelson, L. C. Cantley, and H. Band. 1997. The Cbl phosphotyrosine-binding domain selects a D(N/D)XpY motif and binds to the Tyr292 negative regulatory phosphorylation site of ZAP-70. J. Biol. Chem. 272:33140-33144.

Miura-Shimura, Y., L. Duan, N. L. Rao, A. L. Reddi, H. Shimura, R. Rottapel, B. J. Druker, A. Tsygankov, V. Band, and H. Band. 2003. Cbl-mediated ubiquitinylation and negative regulation of Vav. J. Biol. Chem. 278:38495-38504.

Montesano, R., J. Roth, A. Robert, and L. Orci. 1982. Non-coated membrane invaginations are involved in binding and internalization of cholera and tetanus toxins. Nature 296:651-653.

Naramura, M., H. K. Kole, R.-J. Hu, and H. Gu. 1998. Altered thymic positive selection and intracellular signals in Cbl-deficient mice. Proc. Natl. Acad. Sci. USA 95:15547-15552.

Rao, N., I. Dodge, and H. Band. 2002. The Cbl family of ubiquitin ligases: critical negative regulators of tyrosine kinase signaling in the immune system. J. Leukoc. Biol. 71:753-763.

Rao, N., S. Miyake, A. L. Reddi, P. Douillard, A. K. Ghosh, I. L. Dodge, P. Zhou, N. D. Fernandes, and H. Band. 2002. Negative regulation of Lck by Cbl ubiquitin ligase. Proc. Natl. Acad. Sci. USA 99:3794-3799.

Roose, J. P., M. Diehn, M. G. Tomlinson, J. Lin, A. A. Alizadeh, D. Botstein, P. O. Brown, and A. Weiss. 2003. T cell receptor-independent basal signalingvia Erk and Abl kinases suppresses RAG gene expression. PLoS Biol. 1:E53.

Samelson, L. E. 2002. Signal transduction mediated by the T cell antigen receptor: the role of adapter proteins. Annu. Rev. Immunol. 20:371-394.

Sommers, C. L., J. Lee, K. L. Steiner, J. M. Gurson, C. L. Depersis, D. El-Khoury, C. L. Fuller, E. W. Shores, P. E. Love, and L. E. Samelson. 2005. Mutation of the phospholipase C-γ1-binding site of LAT affects both positive and negative thymocyte selection. J. Exp. Med. 201:1125-1134.

Tanimura, N., M. Nagafuku, Y. Minaki, Y. Umeda, F. Hayashi, J. Sakakura, A. Kato, D. R. Liddicoat, M. Ogata, T. Hamaoka, and A. Kosugi. 2003. Dynamic changes in the mobility of LAT in aggregated lipid rafts upon T cell activation. J. Cell Biol. 160:125-135.

Thien, C. B., F. D. Blystad, Y. Than, A. M. Lew, V. Voigt, C. E. Andoniou, and W. Y. Langdon. 2005. Loss of c-Cbl RING finger function results in high intensity TCR signaling and thymic deletion. EMBO J. 24:3807-3819.

Thien, C. B., D. D. Bowtell, and W. Y. Langdon. 1999. Perturbed regulation of ZAP-70 and sustained tyrosine phosphorylation of LAT and SLP-76 in c-Cbl-deficient thymocytes. J. Immunol. 162:7133-7139.

Thien, C. B., and W. Y. Langdon. 2005. c-Cbl and Cbl-b ubiquitin ligases: substrate diversity and the negative regulation of signalling responses. Biochem. J. 391:153-166.

Thien, C. B., and W. Y. Langdon. 2005. Negative regulation of PTK signaling by Cbl proteins. Growth Factors 23:161-167.

van Leeuwen, J. E., P. K. Paik, and L. E. Samelson. 1999. Activation of nuclear factor of activated T cells-(NFAT) and activating protein 1 (AP-1) by oncogenic 70Z Cbl requires an intact phosphotyrosine binding domain but not Crk(L) or p85 phosphatidylinositol 3-kinase association. J. Biol. Chem. 274:5153-5162.

van Leeuwen, J. E., P. K. Paik, and L. E. Samelson. 1999. The oncogenic 70Z Cbl mutation blocks the phosphotyrosine binding domain-dependent negative regulation of ZAP-70 by c-Cbl in Jurkat T cells. Mol. Cell. Biol. 19: 6652-6664.

Varma, R., G. Campi, T. Yokosuka, T. Saito, and M. L. Dustin. 2006. T cell receptor-proximal signals are sustained in peripheral microclusters and terminated in the central supramolecular activation cluster. Immunity 25:117-127.

Veillette, A., S. Latour, and D. Davidson. 2002. Negative regulation of immunoreceptor signaling. Annu. Rev. Immunol. 20:669-707.

Wilson, B. S., J. R. Pfeiffer, Z. Surviladze, E. A. Gaudet, and J. M. Oliver. 2001. High resolution mapping of mast cell membranes reveals primary and secondary domains of Fc(epsilon)RI and LAT. J. Cell Biol. 154:645-658.

Wu, J. N., and G. A. Koretzky. 2004. The SLP-76 family of adapter proteins. Semin. Immunol. 16:379-393.

Yokosuka, T., K. Sakata-Sogawa, W. Kobayashi, M. Hiroshima, A. Hashimoto-Tane, M. Tokunaga, M. L. Dustin, and T. Saito. 2005. Newly generated T cell receptor microclusters initiate and sustain T cell activation by recruitment of Zap70 and SLP-76. Nat. Immunol. 6:1253-1262.

Yokouchi, M., T. Kondo, A. Houghton, M. Bartkiewicz, W. C. Home, H. Zhang, A. Yoshimura, and R. Baron. 1999. Ligand-induced ubiquitination of the epidermal growth factor receptor involves the interaction of the c-Cb1 RING finger and UbCH7. J. Biol. Chem. 274:31707-31712.

Zhang, W., J. Sloan-Lancaster, J. Kitchen, R. P. Trible, and L. E. Samelson. 1998. LAT: the ZAP-70 tyrosine kinase substrate that links T cell receptor to cellular activation. Cell 92:83-92.

Zhang, W., R. P. Trible, and L. E. Samelson. 1998. LAT palmitoylation: its essential role in membrane microdomain targeting and tyrosine phosphorylation during T cell activation. Immunity 9:239-246.

Zhang, W., R. P. Trible, M. Zhu, S. K. Liu, C. J. McGlade, and L. E. Samelson. 2000. Association of Grb2, Gads, and phospholipase C-γ1 with phosphorylated LAT tyrosine residues. Effect of LAT tyrosine mutations on T cell antigen receptor-mediated signaling. J. Biol. Chem. 275: 23355-23361.

Hershko A, and Ciechanover A.1998. The ubiquitin system. Annu Rev Biochem. 1998; 67:425-79.

Balagopalan L, Barr V A, Sommers C L, Barda-Saad M, Goyal A, Isakowitz M S, and Samelson L E. 2007. c-Cb1-mediated regulation of LAT-nucleated signaling complexes. Mol Cell Biol. 2007 December; 27(24):8622-36.

Hogquist K A, Baldwin T A, Jameson S C. 2005. Central tolerance: learning self-control in the thymus. Nat Rev Immunol. October; 5(10):772-82.

We claim:

1. A composition comprising an isolated, non-naturally occurring linker for activation of T cells (LAT) polypeptide or a fragment thereof, wherein said polypeptide comprises SEQ ID NO: 1 comprising an amino acid substitution of lysine to arginine at amino acid 52 and at amino acid 204, and wherein said polypeptide or fragment thereof exhibits enhanced T cell receptor signaling compared to SEQ ID NO: 1.

2. The composition of claim 1, wherein the polypeptide is in a pharmaceutically acceptable carrier.

3. A kit comprising the composition of claim 1.

* * * * *